United States Patent [19]

Mookherjee et al.

[11] 4,416,902
[45] Nov. 22, 1983

[54] FLAVORING WITH CYCLOHEXENYL-BETA-METHYL ACROLEIN DERIVATIVES

[75] Inventors: Braja D. Mookherjee, Holmdel; Richard A. Wilson, Westfield; Manfred H. Vock, Locust; Michael J. Zampino, North Bergen, all of N.J.

[73] Assignee: International Flavors & Fragrances Inc., New York, N.Y.

[21] Appl. No.: 399,012

[22] Filed: Jul. 16, 1982

[51] Int. Cl.³ .............................. A23L 1/226
[52] U.S. Cl. ........................ 426/3; 426/536; 426/538; 252/522 R; 568/446; 549/295
[58] Field of Search .................. 426/538, 3; 568/446

[56] References Cited

U.S. PATENT DOCUMENTS 3,031,507  4/1962  Ortoli et al. ..................... 260/598
3,313,843  4/1967  Houlihan ......................... 260/473
4,301,184  11/1981  Yoshida et al. ................. 426/538 X
4,374,123  2/1983  Luccarelli et al. .............. 426/538 X

FOREIGN PATENT DOCUMENTS 672025  12/1929  France .

OTHER PUBLICATIONS

Dauphin, "Vilsmeier Formylation of Limonene . . . ", Chem. Communications, Oct. 1979, pp. 799–801.
Arctander Perfume and Flower Chemicals, 1969, vols. I-II, Publ. by the Author, Montclair, N.J., Monograph, Nos. 761-763, 2896.

*Primary Examiner*—Joseph M. Golian
*Attorney, Agent, or Firm*—Arthur L. Liberman

[57] ABSTRACT

Described are the organoleptic uses of the genus of compounds defined according to the structure:

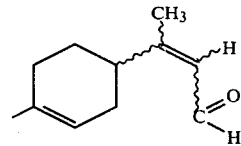

wherein the wavy lines represent the "cis" or "trans" juxtaposition of the methyl, cyclohexenyl, hydrogen and carboxaldehyde moieties around the carbon-carbon double bond, for augmenting or enhancing the flavor and/or aroma of consumable materials including foodstuffs, chewing gums, medicinal products, toothpastes, perfumes, colognes and perfumed articles.

2 Claims, 14 Drawing Figures

GLC PROFILE FOR FRACTION 10 OF EXAMPLE A

NMR SPECTRUM FOR PEAK 10 OF EXAMPLE A.

GLC PROFILE FOR EXAMPLE C.
(CRUDE)

GLC PROFILE FOR EXAMPLE D.

GLC PROFILE FOR EXAMPLE C.

NMR SPECTRUM FOR FRACTION 2 OF EXAMPLE C

GLC PROFILE FOR
FRACTION 2 OF
EXAMPLE D.

GLC PROFILE FOR
FRACTION 1 OF
EXAMPLE C.

GLC PROFILE FOR FRACTION 3 OF EXAMPLE D.

GLC PROFILE FOR FRACTION 3 OF EXAMPLE D.

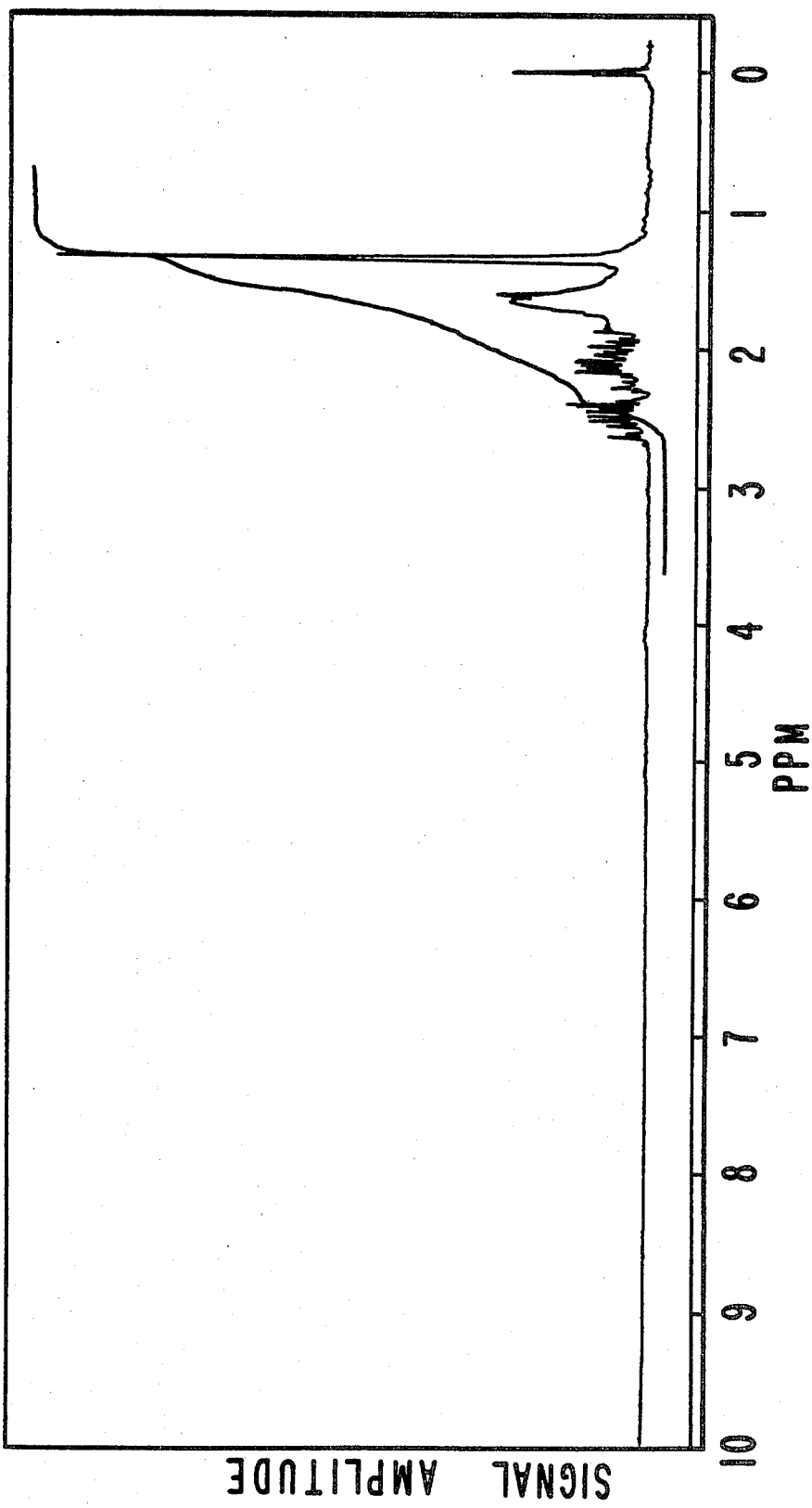
FIG. 14 NMR SPECTRUM FOR PEAK 124 FRACTION 4 OF EXAMPLE C.

FLAVORING WITH CYCLOHEXENYL-BETA-METHYL ACROLEIN DERIVATIVES

BACKGROUND OF THE INVENTION

The instant invention provides the compounds having the structures:

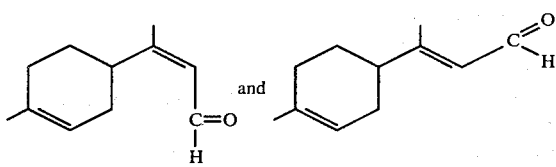

which may also be defined according to the structure:

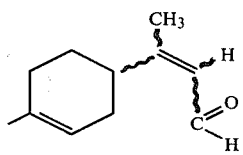

wherein the wavy lines represent the "cis" or "trans" juxtaposition of the methyl, cyclohexenyl, hydrogen and carboxaldehyde moieties around the carbon-carbon double bond, and their uses thereof for their organoleptic properties in augmenting or enhancing the aromas and/or taste of consumable materials.

The materials which provide sweet, bready, lactonic aromas with milky, almond-like, cumin undertones are highly desirable in the art of perfumery. Many of the natural materials which provide such fragrances and contribute such desired nuances to perfumery compositions are high in cost, vary in quality from one batch to another and/or are generally subject to the usual variations of natural products.

By the same token, materials which can provide sweet, fatty, nutty, buttery/lactone, coconut, aldehydic, lemon-like and orange aroma profiles and sweet, fatty, nutty, butter/lactone, coconut-like, aldehydic and orange-like taste profiles are highly desirable in the art of flavoring for foodstuffs, chewing gums, toothpastes, medicinal products and chewing tobaccos. Many of the natural materials which provide such flavor notes and contribute such desired nuances to flavorant compositions are high in cost, vary in quality from one batch to another and/or are generally subject to the usual variations of natural products.

There is, accordingly, a continuing effort to find synthetic materials which will replace, enhance or augment the essential flavor and fragrance notes provided by natural essential oils or compositions thereof. Unfortunately, many of these synthetic materials either have the desired nuances only to a relatively small degree or else contribute undesirable or unwanted odor to the compositions. The search for materials which can provide a more refined coconut-like flavor, for example, has been difficult and relatively costly in the areas of both natural products and synthetic products.

Artificial flavoring agents for foodstuffs have received increasing attention in recent years. For many years such food flavoring agents have been preferred over natural flavoring agents at least in part due to their diminished cost and their reproducible flavor qualities. For example, natural food flavoring agents such as extracts, concentrates and the like are often subject to wide variations due to changes in quality and type and treatment of raw materials. Such variations can be reflected in the end products and result in unfavorable flavor charcteristics in said end products. Additionally the presence of the natural product in the ultimate food may be undesirable because of increased tendency to spoil. This is particularly troublesome in food and food uses where such products as dips, soups, chips, sausages, gravies, dairy desserts and the like are apt to be stored prior to use.

The fundamental problem in creating artificial flavoring agents is that the artificial flavor to be achieved be as natural as possible. This generally proves to be a difficult task since the mechanism for flavor development in many foods, medicinal products, chewing gums and toothpastes is not completely known. This is particularly noticeable in products having coconut-like or fruity (citrusy) flavor characteristics.

Even more desirable are products which can serve as substitutes for difficult to obtain and natural perfumery oils and, at the same time, substitute for natural flavoring ingredients in foodstuffs, chewing gums, medicinal products and toothpastes and chewing tobaccos.

The compounds defined according to the structure:

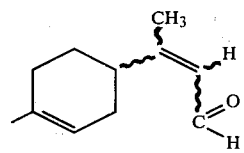

wherein the wavy lines represent the "cis" or "trans" juxtaposition of the methyl, cyclohexenyl, hydrogen and carboxaldehyde moieties around the carbon-carbon double bond, are indicated to be produced according to the paper by Dauphin, Kim Communications, October 1979, pages 799-801 (title: "Vilsmeier Formylation of Limonene A New Method For The Synthesis of Alfa-Atlantone") according to the reaction:

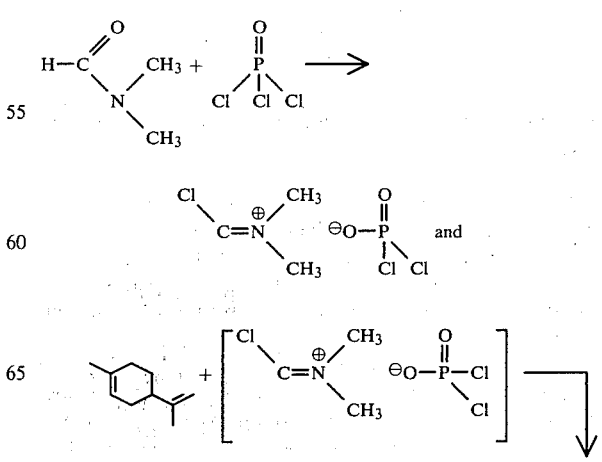

-continued

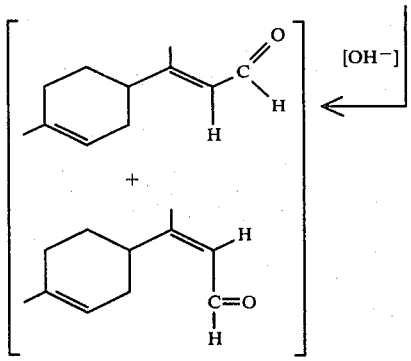

wherein the compound having the structure:

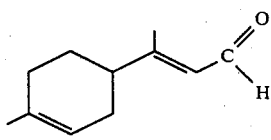

is produced in a ratio to the compound having the structure:

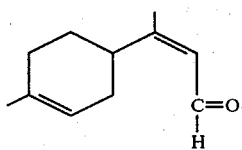

of 40:1.

Cyclohexenyl acrolein derivative are known in the perfume and flavor arts for augmenting or enhancing the aroma or taste of foodstuffs, chewing gums, perfumes and the like.

Thus, Arctander "Perfume and Flavor Chemicals (Aroma Chemicals)" at Volume II, at monograph 2896 discloses the use of the compound having the structure:

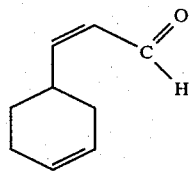

for augmenting or enhancing the aroma of perfumes. Arctander states:

"The subject material has found some application in perfumery, and so has the Cyclohexene carboxaldehyde from which it is made. The parent cyclic aldehyde has a powerful greenleafy odor, and it was interesting to see what type odor could be obtained by the Claisen condensation.

"Although rarely offered under its proper chemical name, this material is still used in various perfume specialties and bases for its refreshing, green note, sometimes useful in Citrus compositions, but also used in Chypres, Fougères, etc. in a combination with Oakmoss, Lavender, etc.

"Prod.: from Acrolein and Butadiene to make Cyclohex-3-enealdehyde. By condensation (Claisen) with Acetaldehyde the title material is obtained. . . .

"The title aldehyde . . . was developed many years ago in a continuation of the search for interesting aldehydes from the Claisen reaction, by which Cinnamic aldehyde had been produced. It was also based upon a new method of obtaining Cyclohexene aldehydes and homologues of same."

Arctander, at monograph 2896, refers to the French Patent No. 672,025 published on Dec. 21, 1929 which discloses the Diels Alder reaction of a number of conjugated dienes with acrolein derivatives to produce cyclohexene carboxaldehydes according to, for example, the reaction:

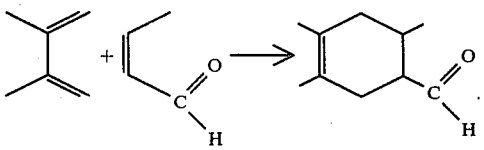

Said French Patent No. 672,025 further discloses at page 3, lines 79–82 and at page 4, lines 1–5, that aldehydes can be reacted with ketones such as acetone or methyl ethyl ketone to produce other compounds of the type "irone".

Arctander "Perfume and Flavor Chemicals (Aroma Chemicals)", Volume I, at monographs 762 and 763, discloses the organoleptic uses of alpha-Cyclocitrylidene Acid Aldehyde (monograph 762) and beta-Cyclocitrylidene Acid Aldehyde (monograph 763) having the structures, respectively:

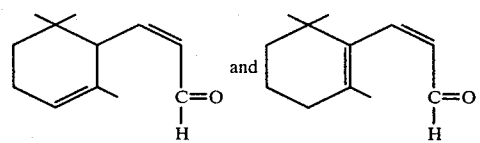

With respect to alpha-Cyclocitrylidene Acetaldehyde having the structure:

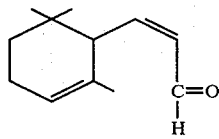

Arctander states:

"Mild floral-woody, somewhat oily-herbaceous odor, remotely reminiscent of Rose with similarity to the odor of hydrogenated Ionones.

"Suggested for use in perfume compositions. It brings a certain amount of floral lift to Rose compositions, and performs fairly well even in soap. However, the cost of the rarely offered and never readily available lots are rather discouraging to the perfumer, and it is most conceivable that this material can be left out of the perfumer's library without any great loss.

"Produced from alpha-Cyclocitral and Acetaldehyde by condensation."

As to beta-Cyclocitrylidene Acetaldehyde having the structure:

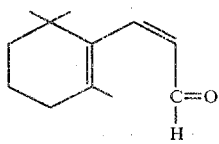

Arctander states:

"Sweet-woody, rather heavy odor, resembling that of beta-Ionone. More fruity than really floral, but not as tenacious as the Ionone.

"Suggested for use in perfume compositions, but since it does not offer any new or unusual odor characteristics, and it cannot be produced in economical competition to beta-Ionone, there is little or no chance that it will ever become a standard shelf ingredient for the perfumer.

"Produced from beta-Cyclocitral and Acetaldehyde by condensation."

Gamma cyclohexyl crotonaldehyde is disclosed to be useful in perfumery in U.S. Pat. No. 3,031,507 issued on Apr. 24, 1962. Gamma cyclohexyl crotonaldehyde has the structure:

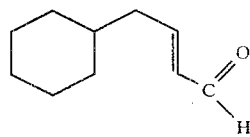

Cinnamic aldehyde is well known in perfumery and substituted homologues thereof are known as intermediates for producing other useful compounds as shown by U.S. Pat. No. 3,313,843 disclosing compounds having the structure:

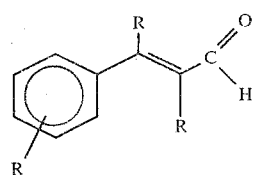

wherein R can be alkyl or hydrogen, useful as intermediates in producing other compounds.

Nothing in the prior art however discloses the organoleptic utility of the compounds defined according to the structure:

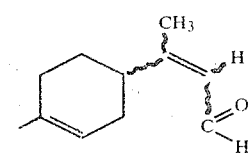

and nothing in the prior art indicates the unexpected, unobvious and advantageous uses of such compounds having the structure:

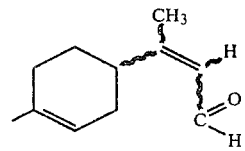

wherein the wavy lines represent the "cis" or "trans" juxtaposition of the methyl, cyclohexenyl, hydrogen and carboxaldehyde moieties around the carbon-carbon double bond, for augmenting or enhancing the flavor and/or aroma of consumable materials including foodstuffs, chewing gums, medicinal products, toothpastes, perfumes, colognes and perfumed articles.

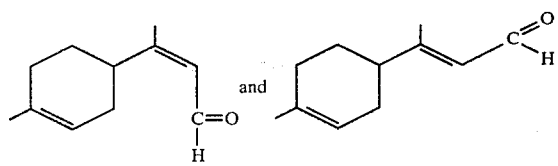

Figure 1:
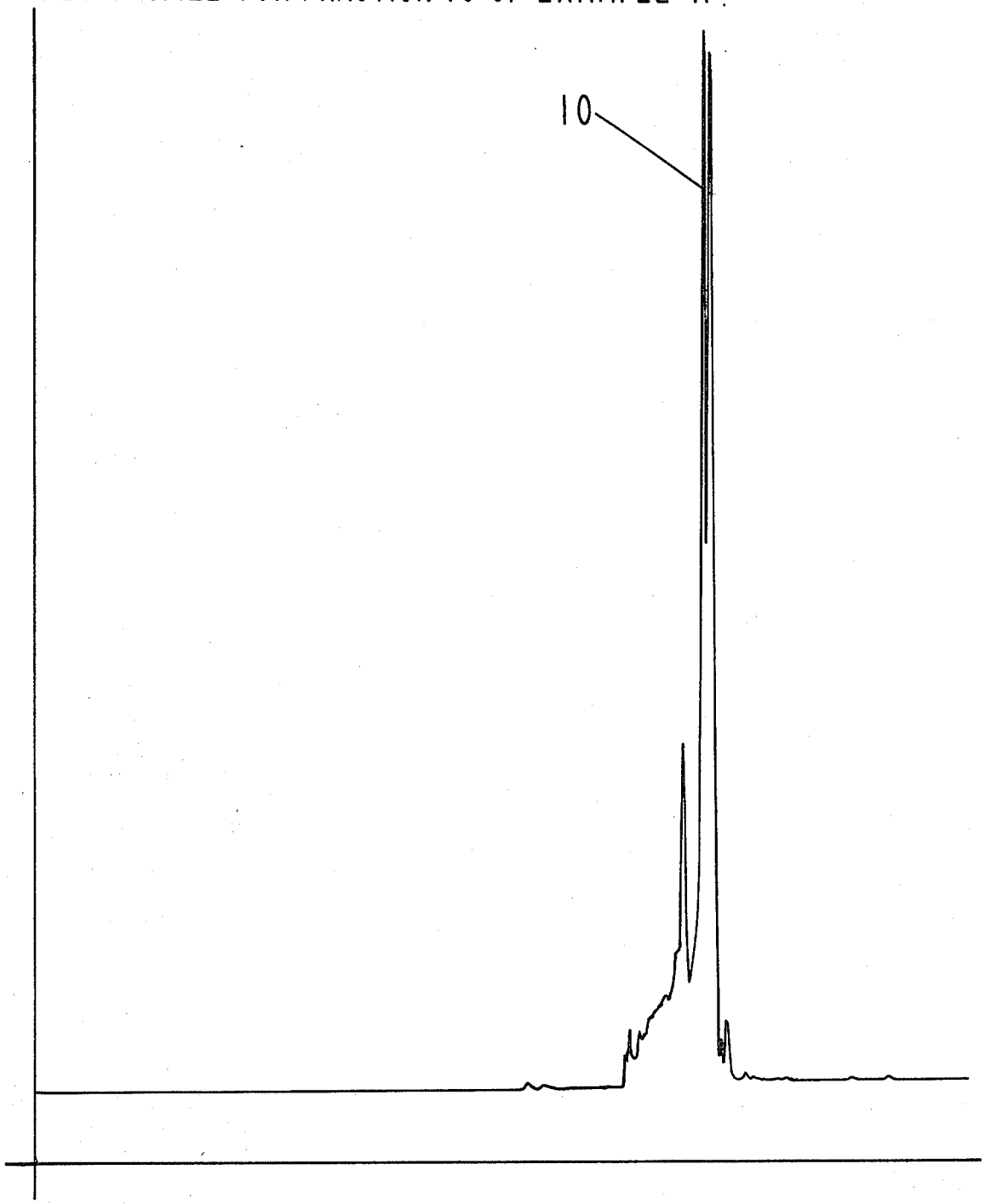
FIG. 1 is the GLC profile for Fraction 4 of the distillation product of the reaction product of Example B containing the compounds having the structures.
Figure 2:
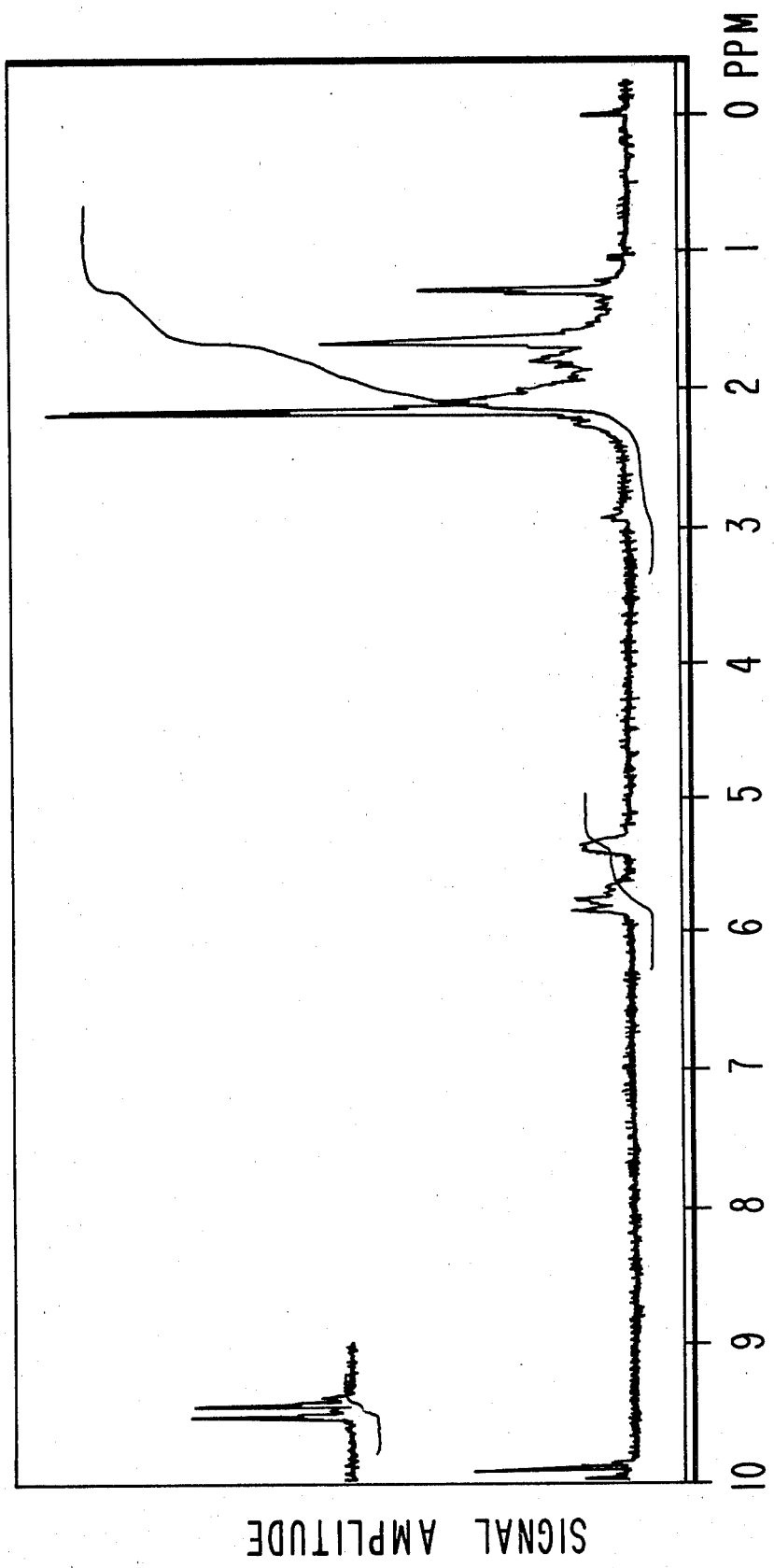

FIG. 2 is the NMR spectrum for the peak indicated by reference numeral "10" on the GLC profile of FIG. 1 for the compounds having the structures:

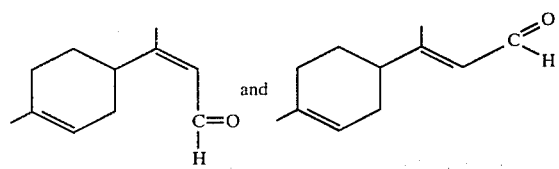

Figure 3:
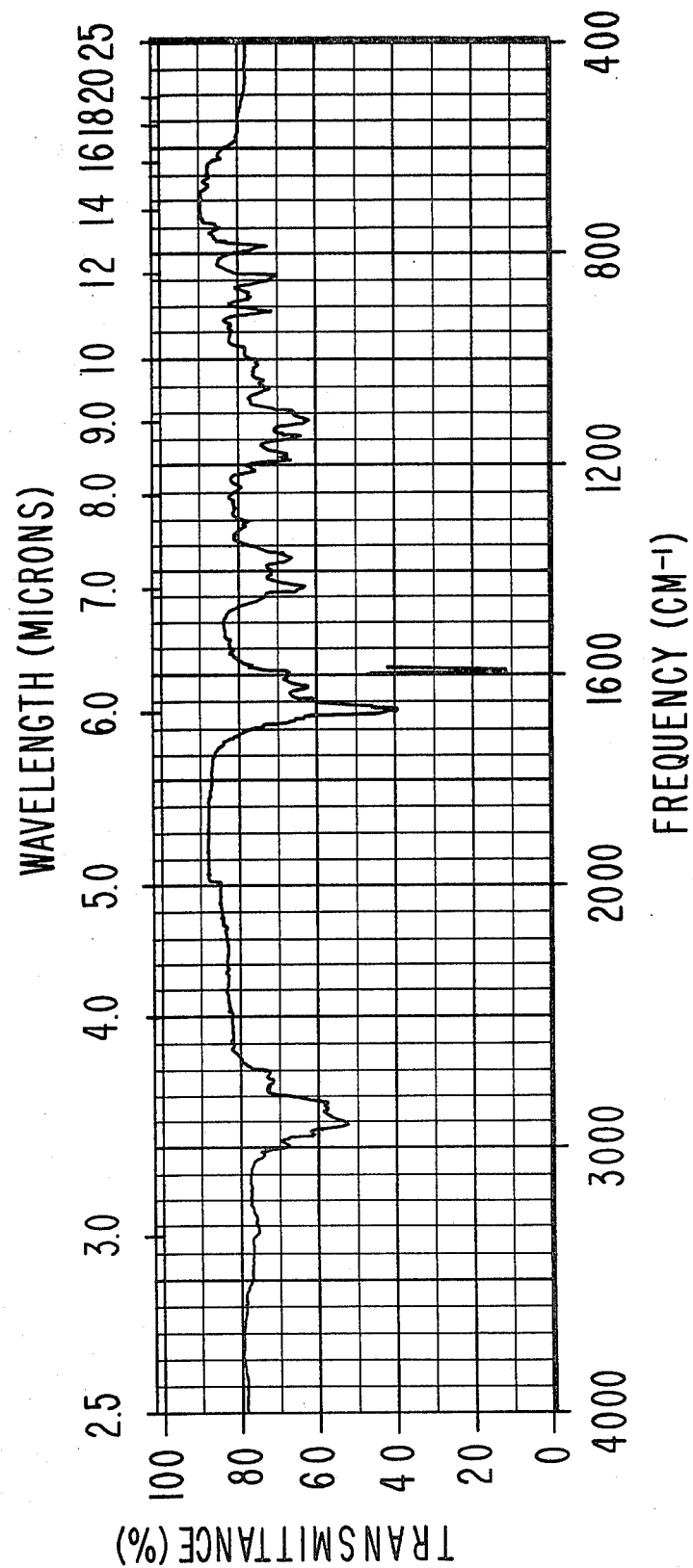

FIG. 3 is the infra-red spectrum for the compounds of the peak indicated by the reference numeral "10" on the GLC profile of FIG. 1, said compounds having the structures:

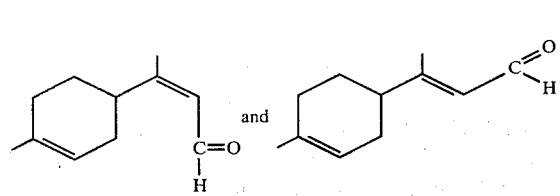

Figure 4:
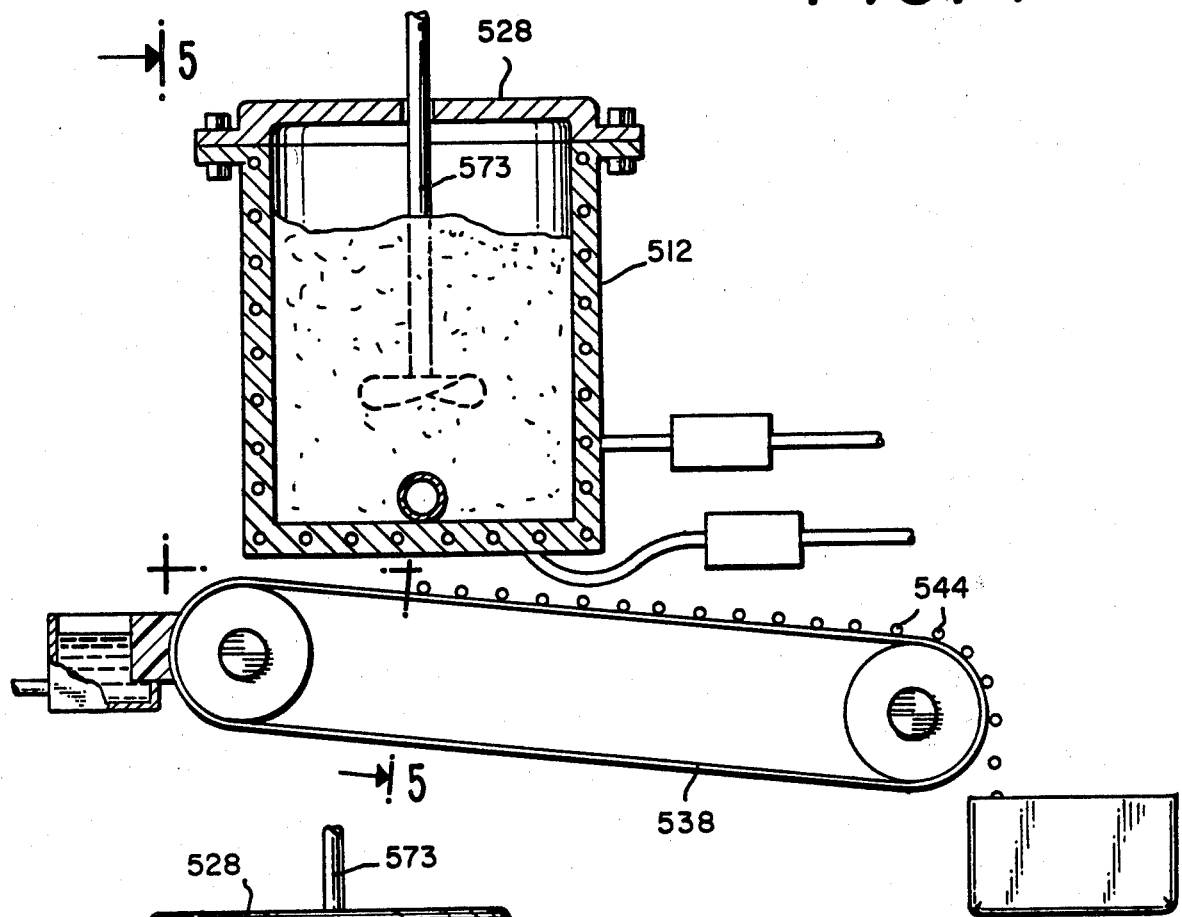

FIG. 4 is a cut-away side elevation view of apparatus used in preparing perfume-containing polymers of our invention.

Figure 5:
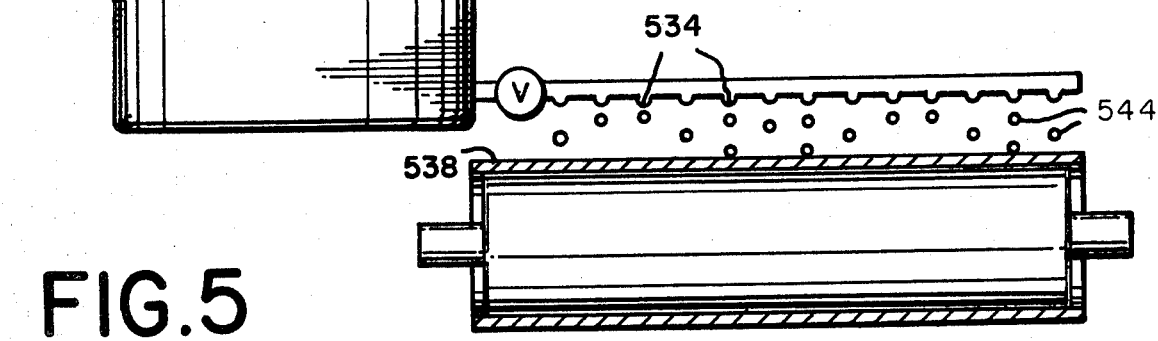

FIG. 5 is a cross-sectional view taken along lines 5—5 of FIG. 4.

Figure 6:
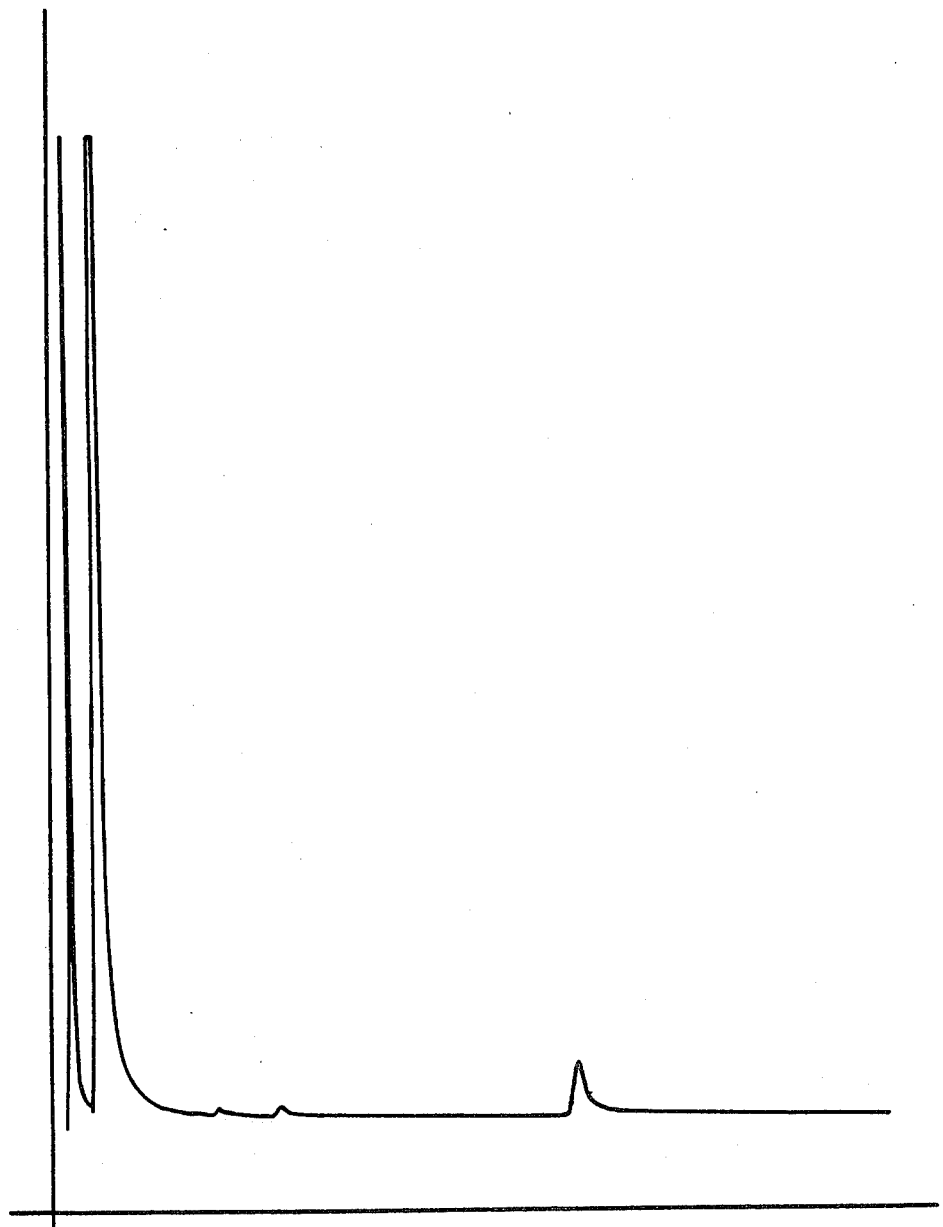

FIG. 6 is the GLC profile for the crude reaction product prior to distillation of the reaction product of Example "C" containing gamma methyl gamma cyclohexyl butyrolactone having the structure:

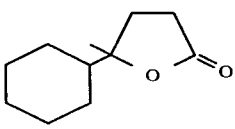

Figure 7:
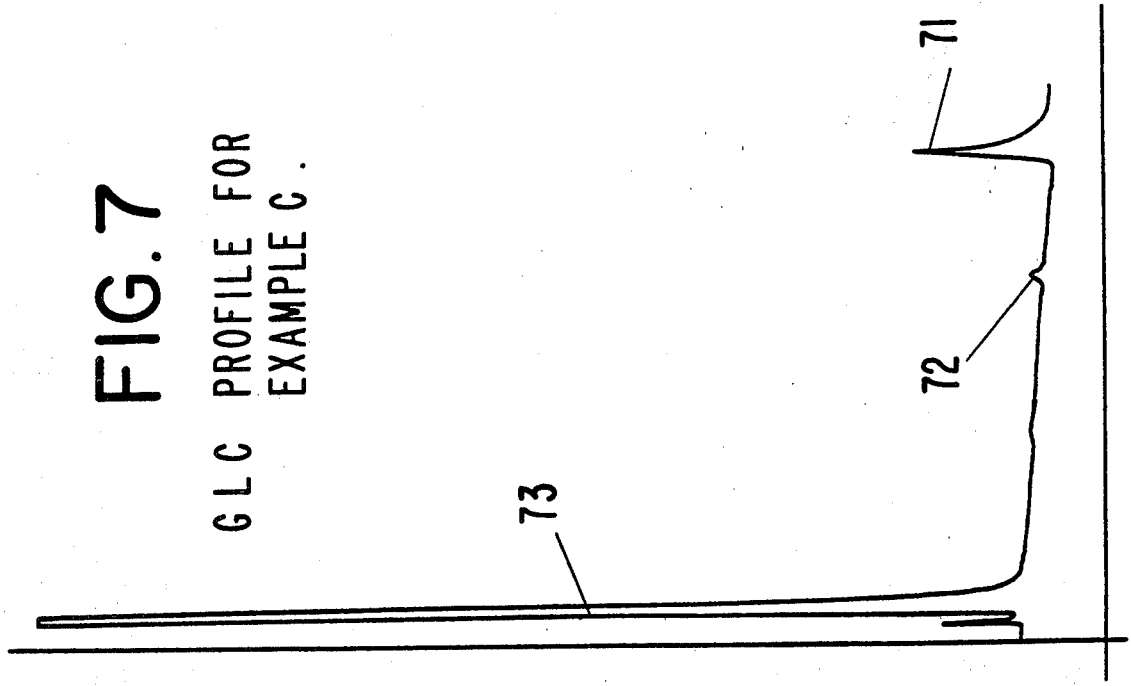

FIG. 7 is the GLC profile for the distillation product of the reaction product of Example "C" containing the compound having the structure:

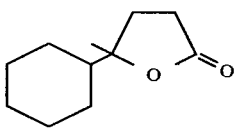

Figure 8:
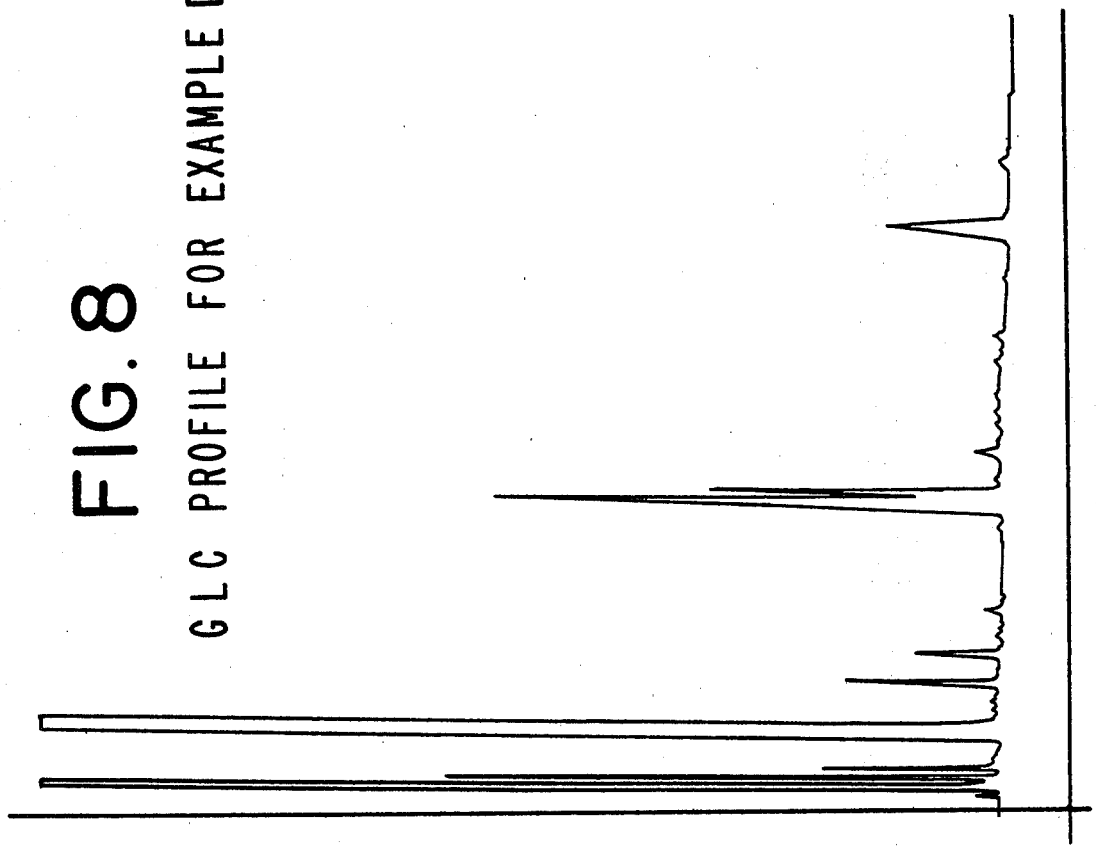

FIG. 8 is the NMR spectrum for fraction 2 of the distillation product of the reaction product of Example "C" containing the compound having the structure:

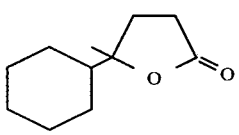

Figure 9:
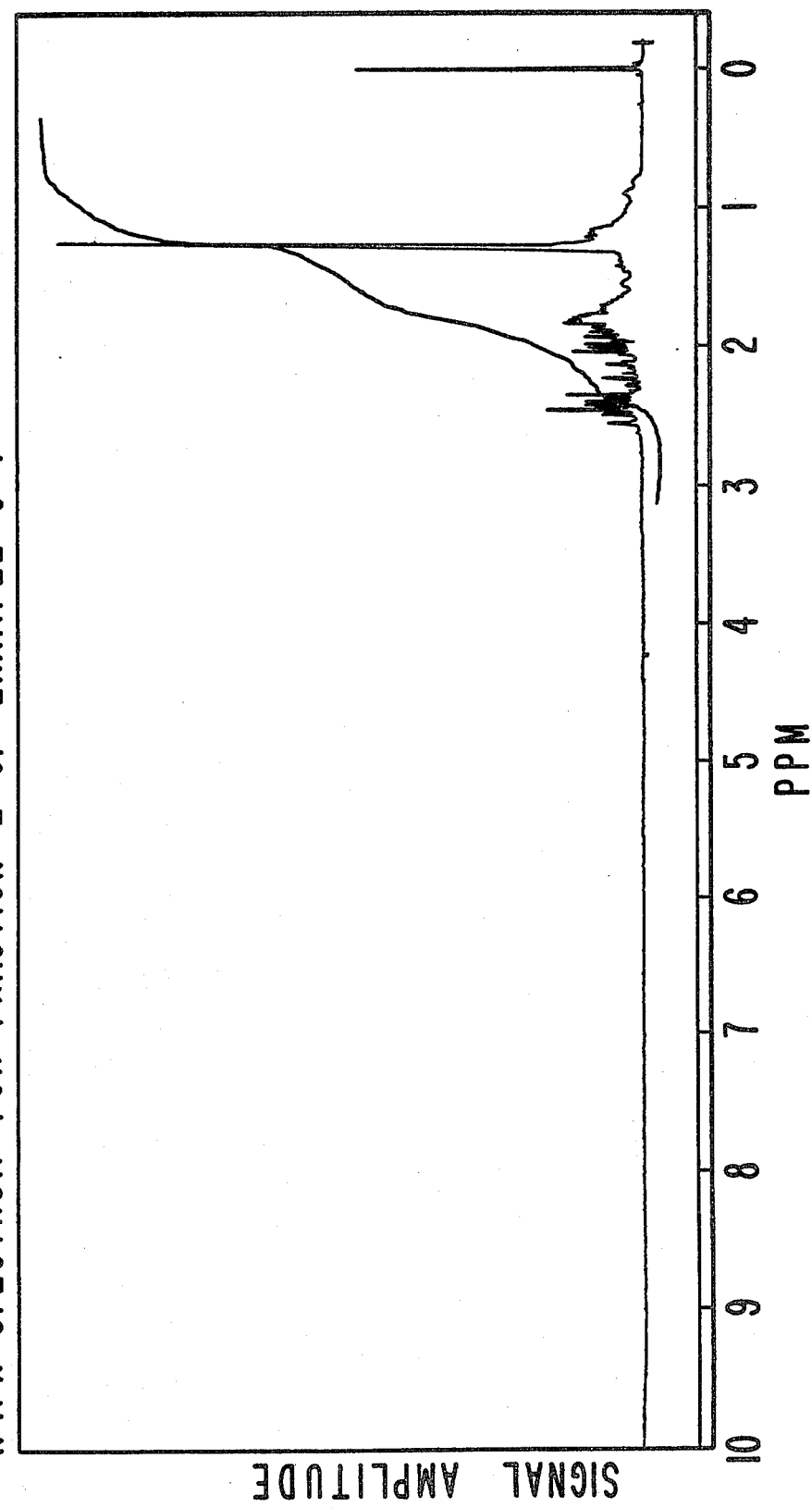

FIG. 9 is the GLC profile for the reaction product of Example "D" containing the compound having the structure:

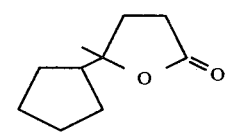

Figure 10:
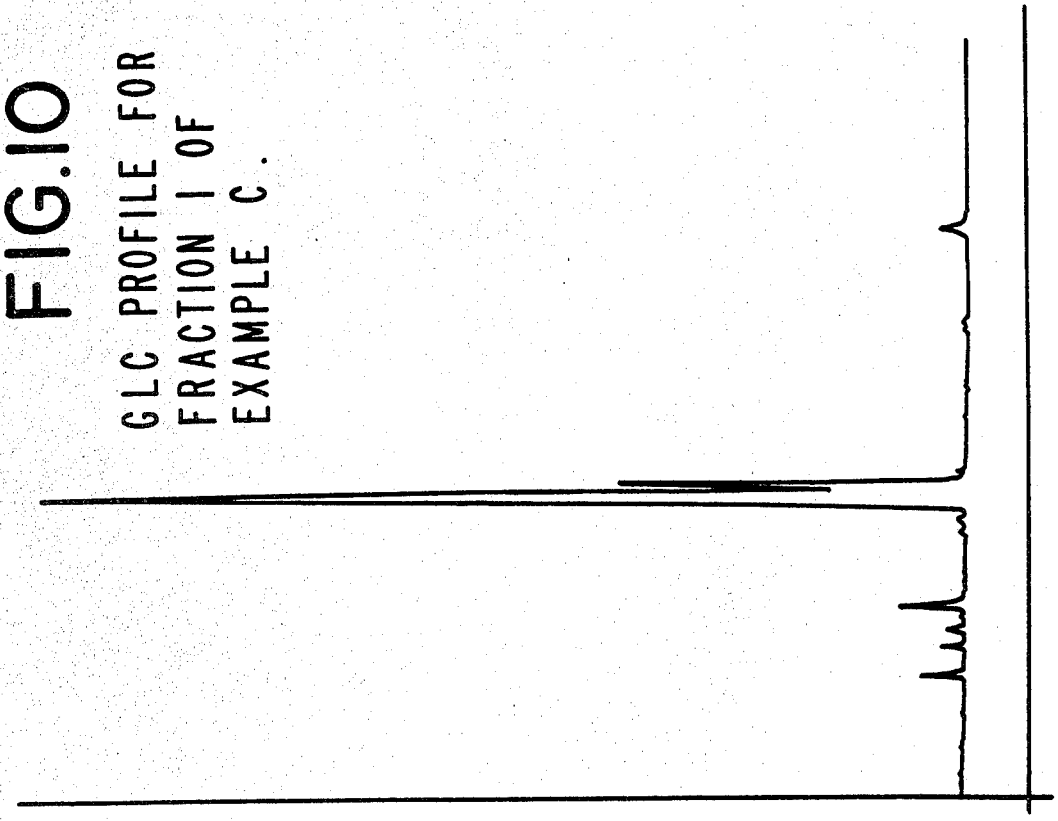

FIG. 10 is the GLC profile for fraction 1 of the distillation product of the reaction product of Example "D" containing the compound having the structure:

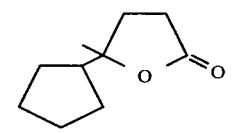

Figure 11:
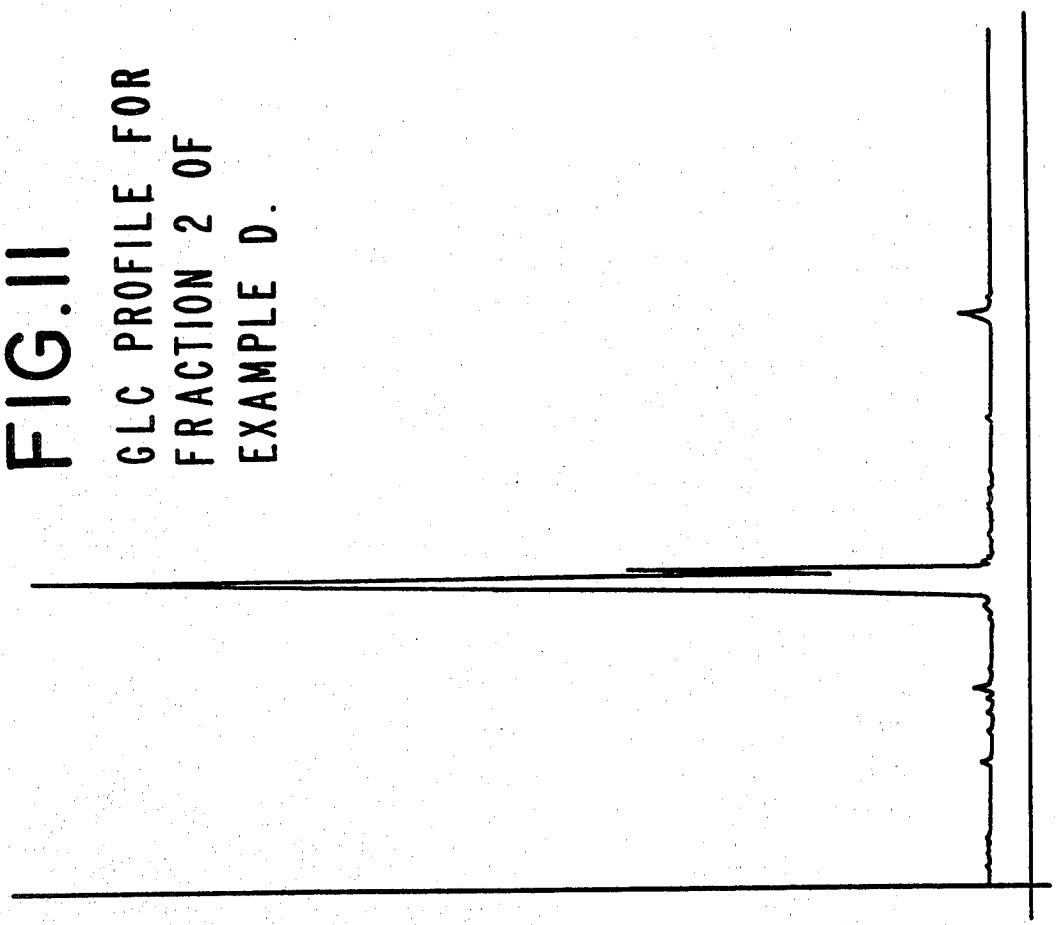

FIG. 11 is the GLC profile for fraction 2 of the distillation product of the reaction product of Example "D" containing the compound having the structure:

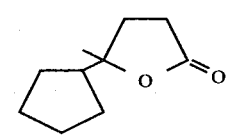

Figure 12:
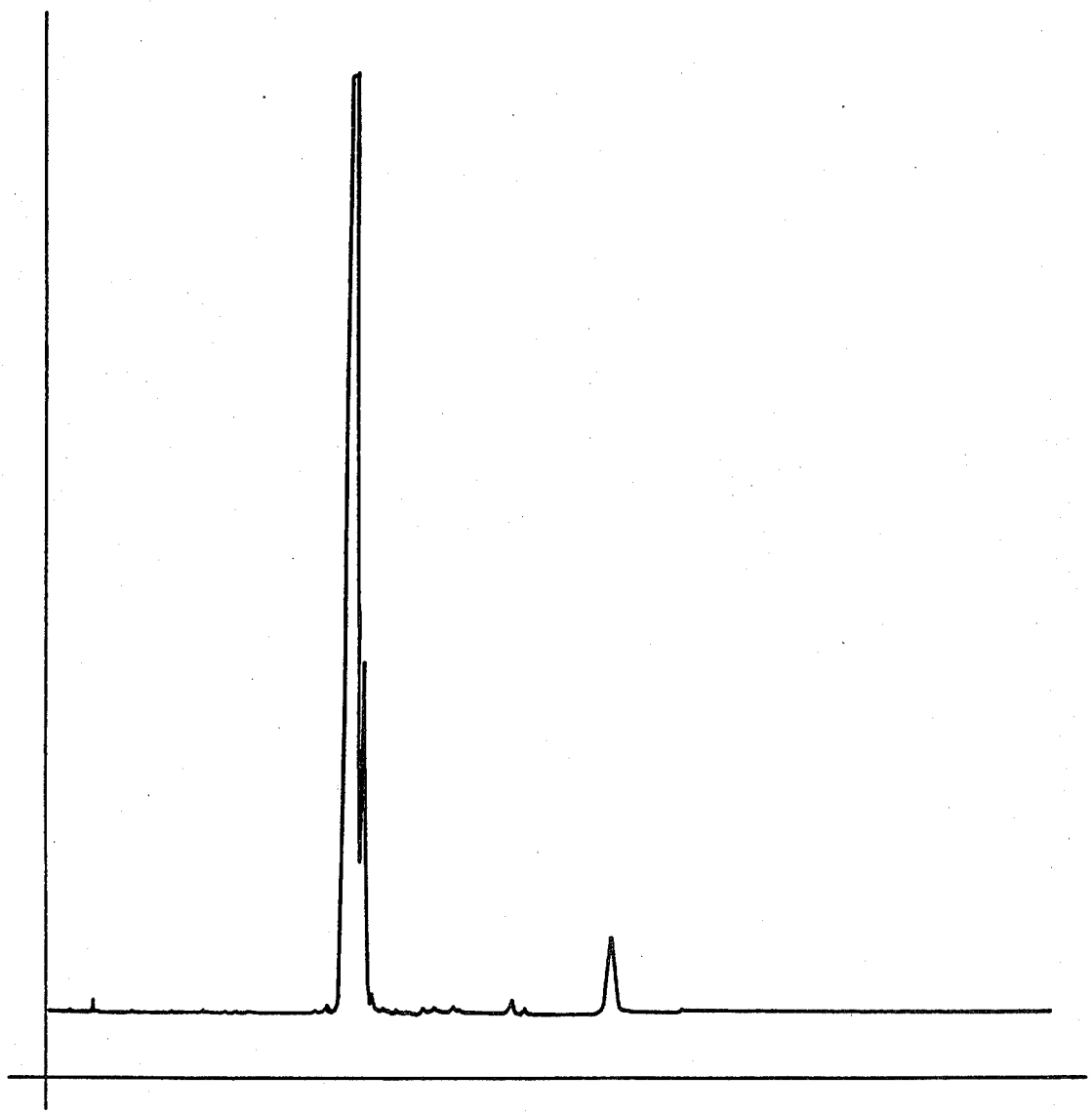

FIG. 12 is the GLC profile for fraction 3 of the distillation product of the reaction product of Example "D" containing the compound having the structure:

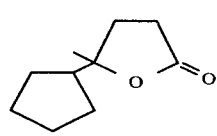

Figure 13:
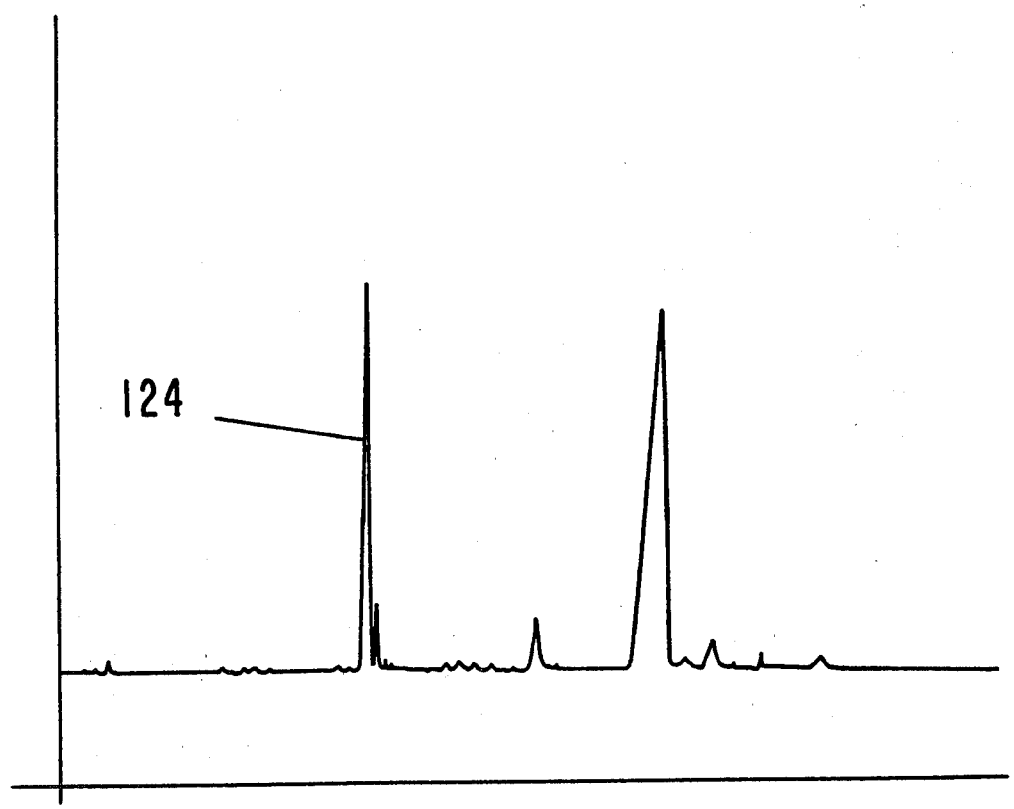

FIG. 13 is the GLC profile for fraction 4 of the distillation product of the reaction product of Example "D" containing the compound having the structure:

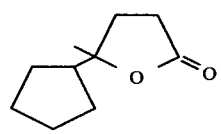

FIG. 14 is the NMR spectrum for the peak designated by reference numeral "124" on the GLC profile for FIG. 13 which is the GLC profile for Fraction 4 of the distillation product of the reaction product of Example "D" containing the compound having the structure:

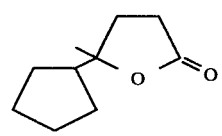

DETAILED DESCRIPTION OF THE DRAWINGS

FIG. 1 is the GLC profile for Fraction 4 of the distillation product of the reaction product of Example "B" containing the compounds having the structures:

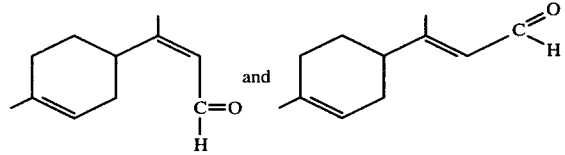

The conditions for obtaining this GLC profile: SE30, 400'×0.032"; column programmed at 100°–190° C. at 4° C. per minute. The peaks indicated by the reference numeral "10" are for the compounds having the structures:

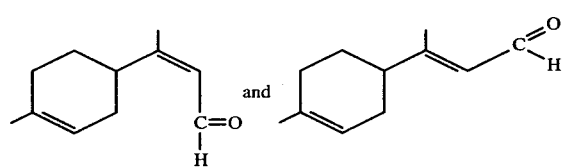

The majority of isomers in these peaks is the "Z" isomer defined according to the structure:

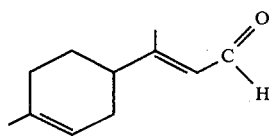

Referring to FIGS. 4 and 5, a thermoplastic polymer, e.g., polyethylene is heated to about 220°–250° F. in a container 512 of the kind illustrated in FIGS. 4 and 5. A fragrance formulation, containing the compounds having the structures:

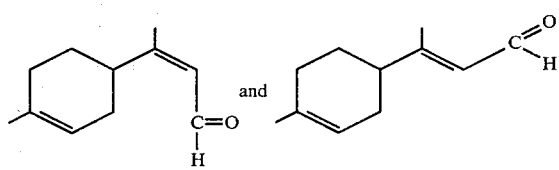

is then quickly added to the liquified thermoplastic polymer, the lid 528 is put in place and the agitating means 573 are actuated. The temperature is maintained at about 225° F. and the mixing is continued for about 5–15 minutes. The valve "V" is then opened to allow flow of the molten thermoplastic polymer enriched with the fragrance containing the compounds having the structures:

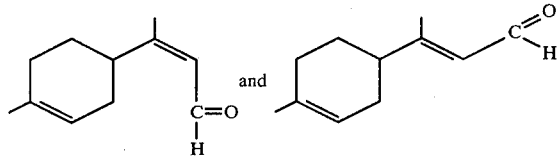

to exit through the orifices 534. The liquid falling through the orifices 534 solidifies almost instantaneously upon impact with the moving cooled conveyor 538. The thermoplastic polymer beads or pellets 544 having a pronounced aroma (e.g., coconut aroma) are thus formed. These pellets are further utilized as set forth in the specific examples, infra.

FIG. 7 is the GLC profile for Fration 2 of the distillation product of the reaction product of Example "C" containing the compound having the structure:

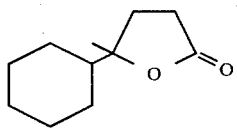

The peak designated by the reference numeral "71" is the peak which designates the compound having the structure:

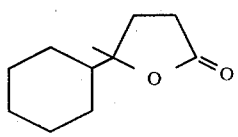

The peak designated by the reference numeral "72" is the peak for ethyl levulinate having the structure:

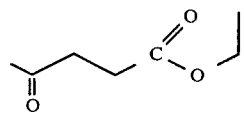

The peak designated by the reference numeral "73" is the peak for acetone.

The conditions for the GLC trapping are: SE-30, 8'×¼", column programmed at 100°–220° C. at 8° C. per minute.

FIG. 13 is the GLC profile for fraction 4 of the distillation product of the reaction product of Example "D" containing the compound having the structure:

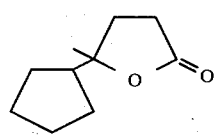

The conditions for the GLC trapping are: SE-30 column, 10'×⅛"; programmed at 100°–220° C. per minute. The peak designated by the reference "124" is the peak for the product having the structure:

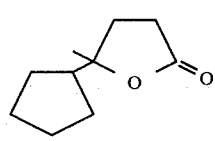

THE INVENTION

This invention relates to limonene carboxaldehydes defined according to the structure:

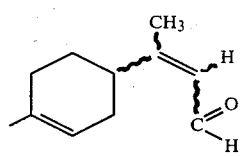

wherein the wavy lines represent the "cis" or "trans" juxtaposition of the methyl, cyclohexenyl, hydrogen and carboxaldehyde moieties around the carbon-carbon double bond, for augmenting or enhancing the flavor and/or aroma of consumable materials including foodstuffs, chewing gums, medicinal products, toothpastes, perfumes, colognes and perfumed articles which include the "cis" and "trans" isomers defined according to the structures:

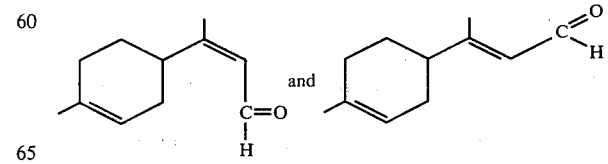

and which also include "endo" and "exo" isomers, for example, the isomers having the structures:

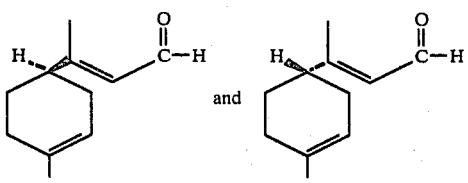
and and uses thereof in augmenting or enhancing a variety of flavors and fragrances in various consumable materials. Briefly, our invention contemplates augmenting or enhancing the flavors and/or fragrances of such consumable materials as perfumes, perfumed articles (e.g., solid or liquid anionic, cationic, nonionic or zwitterionic detergents, cosmetic powders, hair preparations such as shampoos and perfumed thermoplastic and thermoset resins), colognes, foodstuffs, chewing gums, toothpastes, medicinal products and chewing tobaccos, by adding thereto a small but effective amount of at least one of the limonene carboxaldehydes defined according to the structure:

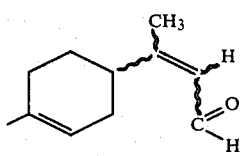

wherein the wavy lines represent the "cis" or "trans" juxtaposition of the methyl, cyclohexenyl, hydrogen and carboxaldehyde moieties around the carbon-carbon double bond, for augmenting or enhancing the flavor and/or aroma of consumable materials including foodstuffs, chewing gums, medicinal products, toothpastes, perfumes, colognes and perfumed articles.

The limonene carboxaldehydes of our invention augment or enhance sweet, bready, lactonic aromas with milky, almond-like, and cumin understones in perfumes, perfumed articles and colognes.

The limonene carboxaldehydes of our invention augment or enhance sweet, fatty, nutty, butter/lactone, coconut-like, aldehydic, lemon-like and orange aroma nuances and sweet, fatty, nutty, butter/lactone, coconut, aldehydic and orange taste nuances of foodstuffs, chewing gums, toothpastes, medicinal products and chewing tobaccos.

Depending upon the method used to prepare the compounds having the structures:

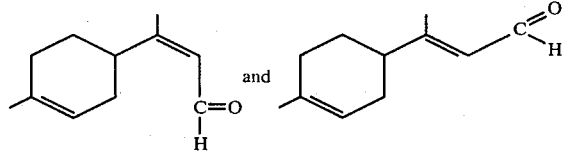
and the aroma and taste nuances of the resulting isomer mixture will differ in a number of respects.

The limonene carboxaldehydes of our invention can be produced according to one of two techniques:

a. By means of a Vilsmeier formylation of limonene according to the reactions:

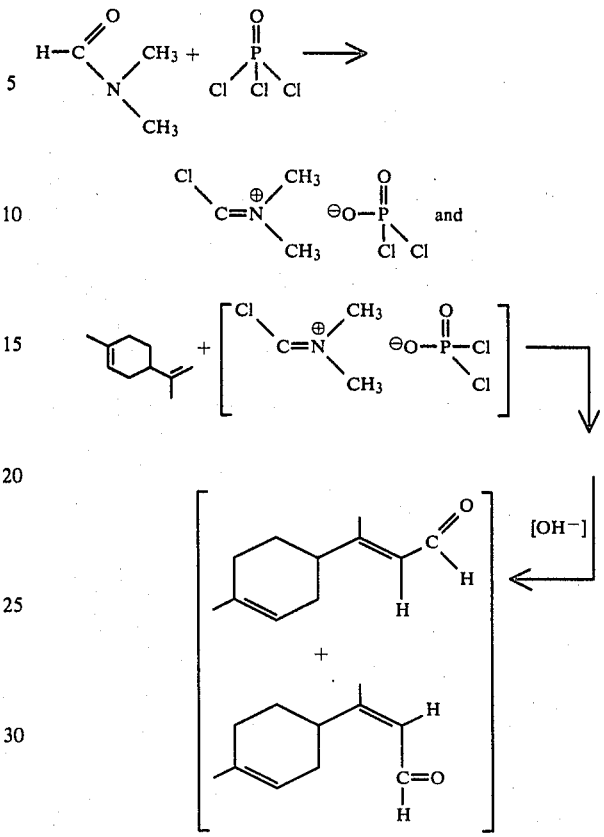

b. According to the reaction sequence:

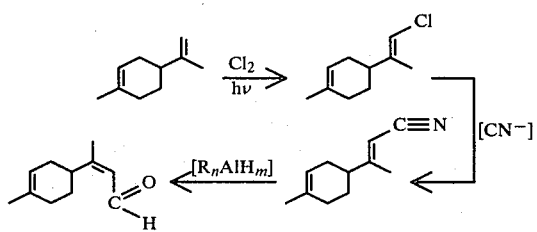

wherein R is lower alkyl and wherein m is 1 or 2 and n is 1 or 2 and the sum: m+n is 3.

Thus, the limonene carboxaldehyde isomer mixture produced according to the reaction sequence:

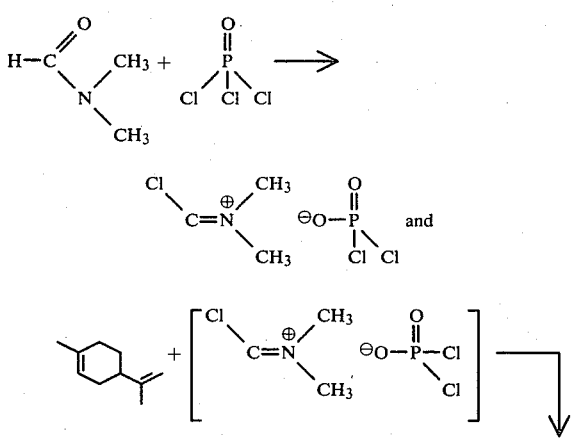

-continued

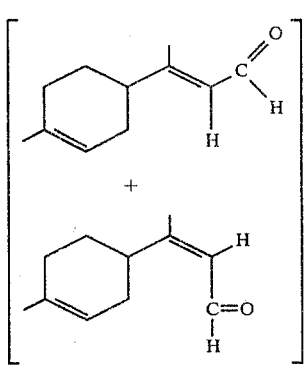

(the Vilsmeier formylation) yields a mixture of isomers having aldehydic, buttery-like, lemon-like and orange aroma nuances and aldehydic, buttery, coconut and orange taste nuances at 0.2 ppm causing this mixture of isomers to be useful in orange juice, buttery, coconut and dairy flavors.

On the other hand, the limonene carboxaldehydes produced according to the reaction sequence:

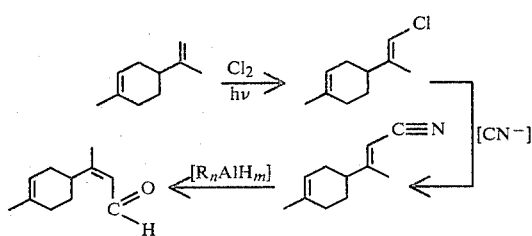

yields a sweet, fatty, nutty, buttery/lactone-like and coconut aroma and taste profile at 0.5 ppm and also yields a sweet, bready, lactonic aroma profile for purpose of perfume and perfumed article utilities.

In addition, the limonene carboxaldehydes defined according to the structures:

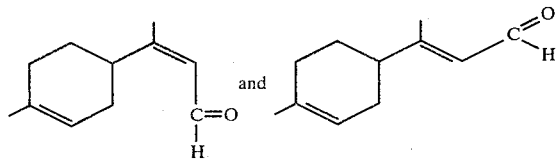

of our invention can be combined with cycloalkyl butyrolactones described in application for U.S. patent Ser. No. 322,873 filed on Nov. 19, 1981 (now abandoned) the specification for which is incorporated by reference herein. These gamma methyl gamma cycloalkyl butyrolactones are defined according to the generic structure:

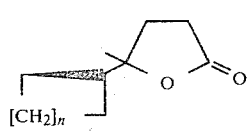

wherein n is 2 or 3. The ratios of the gamma methyl gamma cycloalkyl butyrolactones having the structure:

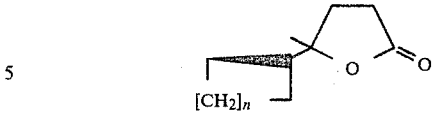

to the limonene carboxaldehyde isomer mixtures of our invention having the structures:

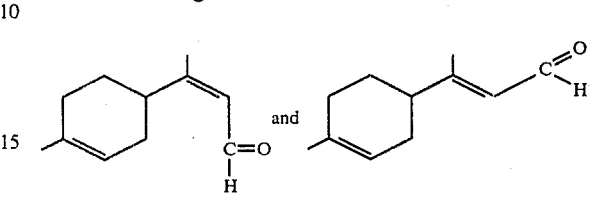

may vary (mole ratio) from 1:99 up to 99:1.

When the limonene carboxaldehydes of our invention are used as food flavor adjuvants, the nature of the co-ingredients included with said gamma methyl gamma cycloalkyl butyrolactones in formulating the product composition will also serve to alter, modify, augment or enhance the organoleptic characteristics of the ultimate foodstuff treated therewith.

As used herein with regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor nuance.

As used herein the term "foodstuff" includes both solid and liquid ingestible materials which usually do but need not have nutritional value. Thus, foodstuffs include soups, convenience foods, beverages, dairy products, candies, vegetables, cereals, soft drinks, snacks and the like.

As used herein the term "medicinal product" includes both solids and liquids which are ingestible, non-toxic materials which have medicinal value such as cough syrup, cough drops, aspirin and chewable medicinal tablets.

The term "chewing gum" is intended to mean a composition which comprises a substantially water insoluble chewable plastic gum base such as chicle or substitutes therefor including jelutong, guttakay rubber or certain comestible natural or synthetic resins or waxes. Incorporated with the gum base in admixture therewith may be plasticizers or softening agents e.g. gelatin and a flavoring composition which incorporates one or both of the limonene carboxaldehydes of our invention, and, in addition, sweetening agents which may be sugars including sucrose or dextrose and/or artificial sweeteners such as cyclamates or saccharine. Other optional ingredients may also be present.

Substances suitable for use herein as co-ingredients or flavoring adjuvants are well known in the art for such use being extensively described in the relevant literature. It is a requirement that any such material be "ingestibly" acceptable and thus non-toxic and otherwise non-deleterious particularly from an organoleptic standpoint whereby the utimate flavor and/or aroma of the consumable material used is not caused to have any unacceptable aroma or taste nuances. Such materials may in general be characterized as flavoring adjuvants or vehicles comprising broadly, stabilizers, thickeners, surface active agents, conditioners, other flavorants and flavor intensifiers.

Stabilizer compounds include preservatives, e.g. sodium chloride; antioxidants, e.g. calcium and sodium ascorbate, ascorbic acid, butylated hydroxyanisole (mixture of 2- and 3-tertiary-butyl-4-hydroxy-anisole), butylated hydroxytoluene (2,6-di-tertiary-butyl-4-methyl phenol), propyl gallate and the like, and sequestrants, e.g. citric acid.

Thickener compounds include carriers, binders, protective colloids, suspending agents, emulsifiers and the like, e.g. agar agar, carrageenan; cellulose and cellulose derivatives such as carboxymethylcellulose and methyl cellulose; natural and synthetic gums such as gum arabic, gum tragacanth; gelatin, proteinaceous materials; lipids, carbohydrates; starches, pectins and emulsifiers, e.g. mono- and diglycerides of fatty acids, skim milk powder, hexoses, pentoses, disaccharides, e.g. sucrose, corn syrup and the like.

Surface active agents include emulsifying agents e.g. fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g. benzoyl peroxide, calcium peroxide, hydrogen peroxide and the like; starch modifiers such as peracetic acid, sodium chlorite, sodium hypochlorite, propylene oxide, succinic anhydride and the like, butters and neutralizing agents, e.g. sodium acetate, ammonium bicarbonate, ammonium phosphate, citric acid, lactic acid, vinegar and the like; colorants, e.g. carminic acid, cochineal, tumeric and curcuma and the like; firming agents such as aluminum sodium sulfate, calcium chloride and calcium gluconate; texturizers, anticaking agents, e.g. aluminum calcium sulfate and tribasic calcium phosphate; enzymes; yeast foods, e.g. calcium lactate and calcium sulfate; nutrient supplements, e.g. iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, henzoic acid, n-butyric acid, caproic acid, caprylic acid, cinnamic acid, isobutyric acid, isovaleric avcid, alpha-methylbutyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methylbutanal, beta,-beta-dimethylacrolein, methyl n-amyl ketone, n-hexanal, 2-hexenal, isopentanal, hydrocinnamic aldehyde, cis-3-hexenal, 2-heptenal, nonyl aldehyde, 4-(p-hydorxyphenyl)-2-butanone, alpha-ionone, beta-ionone, 2-methyl-3-butanone, benzaldehyde, damascone, alpha-damascone, beta-damascone, acetophenone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpin hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl carpylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexeneyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyldiphenyl, methyl naphthalene, myrcene, naphthalene, octadecane, tetradecane, tetramethylnaphthalene, tridecane, trimethylnaphthalene, undecane, caryophyllene, alpha-phellandrene, beta-phellandrene, p-cymene 1-alpha pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methylethylpyrazine, tetramethylpyrazine, trimethylpyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose, capsicum, yara yara and vanilla; other lactones such as gamma-nonalactone, gamma-decalactone, gamma-dodecalactone, gamma-undecalactone, delta-decalactone, delta-dodecalactone, delta-undecalactone; sulfides, e.g. methyl sulfide and other materials such as maltol, ethyl maltol and acetals (e.g. 1,1-diethoxyethane, 1,1-dimethoxyethane and dimethoxymethane), piperazine, chavicine and piperidine.

The specific flavoring adjuvant selected for use may be either solid or liquid depending upon the desired physical form of the ultimate product, i.e. foodstuff, whether simulated or natural, and should, in any event, (i) be organoleptically compatible with the limonene carboxaldehydes of our invention by not covering or spoiling the organoleptic properties (aroma and/or taste) thereof; (ii) be non-reactive with the limonene carboxaldehydes of our invention and (iii) be capable of providing an environment in which the limonene carboxaldehydes of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g. simulated foodstuffs, ingredients capable of providing normally solid compositions should be selected such as various cellulose derivatives.

As will be appreciated by those skilled in the art, the amount of limonene carboxaldehydes of our invention employed in a particular instance can vary over a relatively wide range, depending upon the desired organoleptic effects to be achieved. Thus, correspondingly greater amounts would be necessary in those instances wherein the ultimate food composition to be flavored (e.g. with a coconut flavor) is relatively bland to the taste, whereas relatively minor quantities may suffice for purpose of enchancing the composition merely deficient in natural flavor or aroma. The primary requirement is that the amount selected be effective, i.e. sufficient to alter, modify or enhance the organoleptic characteristics of the parent composition, whether foodstuff per se, chewing gum per se, medicinal product per se, beverage (e.g. alcoholic beverage such as pina colada) toothpaste per se or flavoring composition.

The use of insufficient quantities of limonene carboxaldehydes will, of course, substantially vitiate any possibility of obtaining the desired results while excess quantities prove needlessly costly and, in extreme cases, may disrupt the flavor-aroma balance thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions, alcoholic beverage compositions and toothpaste compositions, it is found that quantities of limonene carboxaldehydes ranging from a small but effective amount, e.g., 0.5 parts per million up to about 100 parts per million based on total composition, are suitable. Concentrations in excess of the maximum quantity stated are not normally recommended since they fail to provide commensurate enchancement or organoleptic properties. In those instances wherein the limonene carboxaldehydes are added to the foodstuff as an integral component of a flavoring composition, it is, of course, essential that the total quantity of flavoring composition employed be sufficient to yield an effective limonene carboxaldehyde concentration in the foodstuff product.

Food flavoring compositions prepared in accordance with the present invention preferably contain the limonene carboxaldehydes in concentrations ranging from about 0.1% up to about 25% by weight based on the total weight of the said flavoring composition.

The compositions described herein can be prepared according to conventional techniques well known as typified by cake batters, alcoholic beverages (e.g. pina colada) and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the limonene carboxaldehydes with, for example, gum arabic, gum tragacanth, xanthan gum, guar gum, carrageenan and the like, and thereafter spray-drying the resultant mixture whereby to obtain the particulate solid product. Pre-prepared flavor mixes in powder form, e.g. a fruit-flavored powder mix or a coconut flavored powder mix or a "pina colada" powder mix are obtained by mixing the dried solid components, e.g. starch, sugar and the like, and the limonene carboxaldehydes in a dry blender until the requisite degree of uniformity is achieved.

It is presently preferred to combine with the limonene carboxaldehydes of our invention the following adjuvants:
oil of nutmeg;
clove oil;
almond oil;
almond paste;
gamma-nonalactone;
gamma-undecalactone;
gamma-decalactone;
gamma-dodecalactone;
delta-dodecalactone;
delta-undecalactone;
delta-decalactone;
delta-nonalactone;
delta-octalactone;
beta-damascenone;
alpha-damascone;
beta-damascone;
acetaldehyde;
acetaldehyde diethylacetal;
acetoxyethoxyethane;
cinnamic alcohol;
cinammic aldehyde;
cinnamic aldehyde diethylacetal;
diethylacetal of 3-phenyl-4-pentenal;
diethylacetal of 2-phenyl-5-hexenal;
n-methylanthranilate;
maltol;
ethylmaltol;
propylmaltol;
2,5-dimethyl-3-hydroxy-4,5-dihydrofuran-4-one; and
2,5-diethyl-3-hydroxy-4,5-dihydrofuran-4-one.

The limonene carboxaldehydes of our invention can be used to contribute sweet, bready, lactonic, coconut-like and citrusy aromas to perfumed articles, perfume compositions and colognes. As olfactory agents, the limonene carboxaldehydes of our invention can be formulated into or used as components of a "perfume composition".

The term "perfume composition" is used herein to mean a mixture of organic compounds including, for example, alcohols, aldehydes, ketones, nitriles, ethers, lactones other than the limonene carboxaldehydes of our invention, and frequently hydrocarbons which are admixed so that the combined odors of the individual components produce a pleasant or desired fragrance. Such perform compositions usually contain; (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) topnotes which are usually low-boiling, fresh-smelling materials.

In perfume compositions, the individual component will contribute its particular olfactory characteristics, but the overall effect of the perfume composition will be the sum of the effects of each of the ingredients. Thus, the individual compounds of this invention or mixtures thereof, can be used to alter the aroma characteristics of a perfume composition, for example, by highlighting or moderating the olfactory reaction contributed by another ingredient in the composition.

The amount of the limonene carboxaldehydes of our invention which will be effective in perfume compositions depends on many factors including the other ingredients, their amounts and the effects which are desired. It has been found that perfume compositions containing as little as 2% of the limonene carboxaldehydes of our invention or even less, can be used to impart an interesting sweet, bready, lactonic, coconut-like and citrusy aroma to soaps, cosmetics, and other products including solid or liquid anionic, cationic, nonionic or zwitterionic detergents and performed plastics. The amount employed can range up to 50% or higher and will depend on considerations of cost, nature of the end product and the effect desired on the finished product and the particular fragrance sought.

The limonene carboxaldehydes of our invention can be used alone or in a perfume composition as an olfactory component in detergents and soaps, space odorants and deodorants; perfumes, colognes, toilet water, bath salts; hair preparations such as lacquers, brilliantines, pomades and shampoos; cosmetic preparations such as creams, deodorants, hand lotions and sun screens; powders such as talcs, dusting powders, face powders and the like. When used as an olfactory component for perfumed articles, as little as 0.01% of the limonene carboxaldehydes of our invention will suffice to impart an interesting, sweet, bready, lactonic, coconut and citrusy aroma profile. Generally no more than 0.5% based on the weight of the perfumed article is required.

In addition, the perfume composition can contain a vehicle or carrier for the limonene carboxaldehydes of our invention taken alone or taken further together with other ingredients. The vehicle can be a liquid such as an alcohol such as ehtanol, a glycol such as propylene glycol or the like. The carrier can be an absorbent solid such as gum or components for encapsulating the composition such as gelatin (as by coacervation) or a urea formaldehyde polymer (for forming polymerized capsules around the central perfume oil which is located within the capsule).

The following examples are given to illustrate embodiments of this invention as it is presently preferred to practice it. It will be understood that these examples are illustrative and that the invention is not to be considered as restricted thereto except as indicated in the appended claims.

EXAMPLE "A"

Preparation of Limonene Carboxaldehydes

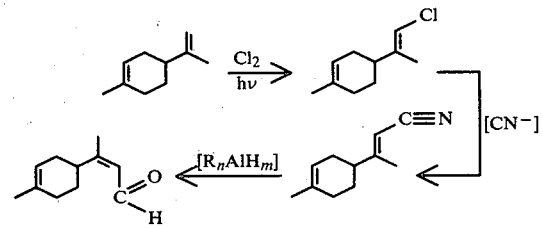

wherein R represents isobutyl; n represents 2 and m represents 1.

Into a 2-liter rection vessel is placed limonene nitrile (200 moles); 25% diisobutyl aluminum hydride in toluene (2.1 moles of diisobutyl aluminum hydride) and 200 ml anhydrous toluene. The reaction mass is stirred at reflux for a period of 4 hours. The reaction mass is then distilled at a vapor temperature of 63°–65° C. at 0.2 mm/Hg pressure to yield a 50:50 mixture of isomers having the structures;

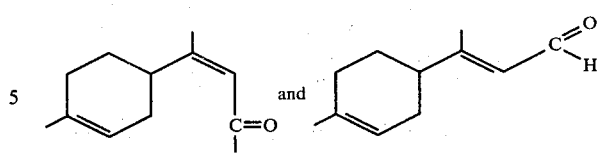

EXAMPLE "B"

Reactions:

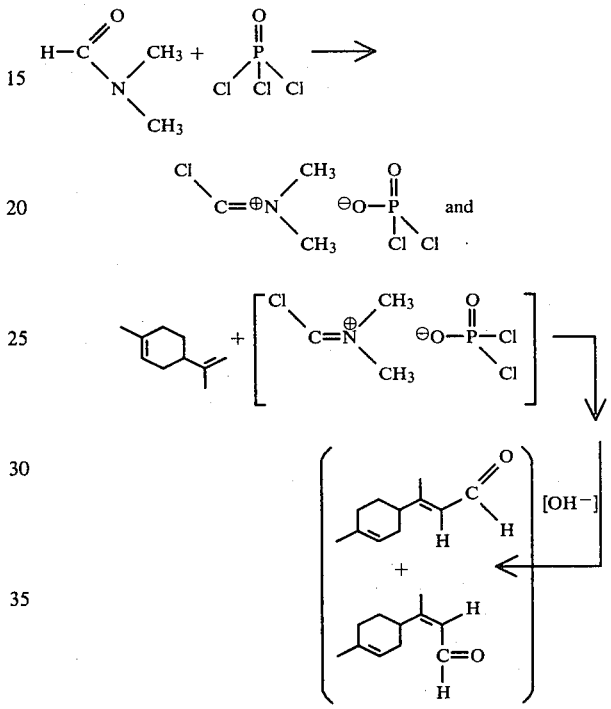

Into a 3-liter reaction flask equipped with over-head stirrer, addition funnel, condenser, nitrogen blanket apparatus and isopropyl alcohbnol dry ice bath is placed 40 grams of dimethylformamide (0.5 moles) in 100 ml methyl dichloride. 76.5 Grams of phosphoryl chloride (0.5 moles) in 50 ml methylene dichloride is added to the solution while maintaining the reaction mass at about 5° C. The mixture is then added to 0.5 moles of 68 grams of limonene dissolved in 250 ml methylene dichloride while maintaining the reaction mass at room temperature. After stirring for a period 6 days, the reaction mass is poured into 1-liter of water, in a separatory funnel. The resulting mixture now exists in two phases; an organic phase and an aqueous phase. The organic phase is separated from the aqueous phase and the aqueous phase is neutralized to a pH of 9 with a 5 molar sodium hydroxide solution. The aqueous phase is then extracted with diethyl either and the extracts are dried and concentrated to 17.4 grams crude reaction product. The resulting material is distilled yielding the following fractions:

| Fraction No. | Vapor Temp. (°C.) | Liquid Temp. (°C.) | Vacuum mm/Hg Pressure | Weight of Fraction |
|---|---|---|---|---|
| 1 | 60/62 | 75/74 | 0.1 | 1.1 |
| 2 | 64 | 76 | 0.15 | 2.6 |
| 3 | 52 | 85 | 0.15 | 1.6 |

-continued

| Fraction No. | Vapor Temp. (°C.) | Liquid Temp. (°C.) | Vacuum mm/Hg Pressure | Weight of Fraction |
|---|---|---|---|---|
| 4 | 65 | 114 | 0.25 | 2.3 |

The resulting distillate is then redistilled on a micro vigreux column yielding the following fractions:

| Fraction No. | Vapor Temp. (°C.) | Liquid Temp. (°C.) | Vaccum mm/Hg Pressure | Weight of Fraction |
|---|---|---|---|---|
| 1 | 57/67 | 85/86 | 0.2 | 0.4 |
| 2 | 56 | 89 | 0.2 | 0.2 |
| 3 | 70 | 88 | 0.2 | 1.2 |
| 4 | 75 | 90 | 0.2 | 1.2 |
| 5 | 72 | 92 | 0.2 | 1.8 |
| 6 | 65 | 95 | 0.2 | 1.0 |

FIG. 1 is the GLC profile for Fraction 4 of the foregoing distillation product: (Conditions: 400'×0.032", SE-30, column programmed at 100°–190° C. at 4° C. per minute). The peaks indicated by reference numeral "10" are the peaks for the reaction products having the structures:

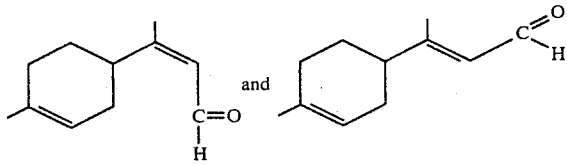

FIG. 2 is the NMR spectrum for the peak indicated by reference numeral "2" on the GLC profile of FIG. 1 (solvent: CFCl$_3$; field strength 100 MHZ).

FIG. 3 is the infra-red spectrum for the peak indicated by reference numeral "10" on the GLC profile of FIG. 1.

The resulting product has an aldehydic, buttery, lemon-like, orange aroma and aldehydic, buttery, coconut and orange-like taste profile at 0.2 ppm insofar as food flavor value is concerned. Insofar as its fragrance value, it has a coconut-like, citrusy aroma and taste profile.

EXAMPLE "C"

Preparation of Gamma Methyl Gamma Cyclohexyl Buttyrolactone

Reaction:

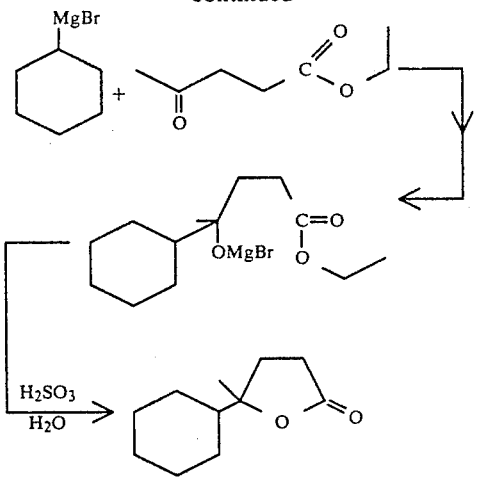

Into a 1 liter reaction flask equipped with nitrogen blanket appartus, stirrer, thermometer, and reflux condenser is added 250 ml anhydrous diethylether and 26.7 grams of magnesium turnings and 2 crystals of iodine. The resulting mixture is heated to reflux at 35° C. and while refluxing, 164 grams of cyclohexyl bromide is added to the mixture. After the cyclohexyl bromide addition is complete, the reaction product is refluxed for a period of 4 hours.

Into a 3-liter reaction flask equipped with stirrer, addition funnel, condenser and cooling bath is added 144 grams of ethyl levulinate and 500 ml of toluene. The resulting mixture is cooled to 0°–5° C. over a period of 2 hours. The cyclohexyl magnesium bromide produced, supra, is added to the resulting mixture while maintaining the temperature at 0°–10° C. At the end of the completion of the addition of the cyclohexyl magnesium bromide, the reaction mass is agitated and refluxed for a period of 1.5 hours.

At this point, 1 liter of 25% aqueous sulfuric acid is added to the reaction mass slowly while maintaining the temperature at 20°–25° C.

The reaction mass is then transferred to a 5 liter speparatory funnel and extracted with two 500 ml portions of toluene. The toluene extracts are then washed as follows:

(a) Two one-liter portions of water
(b) One one-liter portion of 5% aqueous sodium bicarbonate
(c) One one-liter portion of water
(d) One one-liter portion of saturated sodium chloride.

The resulting product is then dried over anhydrous sodium sulfate. The resulting dried material is then distilled at a liquid temperature of 240° C.; a vapor temperature of 195° C.; and a pressure of 18 mm/Hg on a 2" Splash column equipped with saddles.

The resulting product has a pleasant sweet, creamy, coconut-like, macaroon-like aroma and taste profile with green, herbaceous and bitter undertones.

FIG. 6 is the GLC profile of the crude product prior to distillation.

FIG. 7 is the GLC profile of the distillation product. Peak 72 of the GLC profile of FIG. 7 is representative of the ethyl leuvlinate. Peak 71 is representative of the product having the structure:

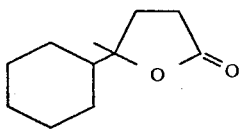

Peak 3 is representative of acetone.

FIG. 8 is the NMR spectrum for Fraction 2 of the foregoing distillation product.

EXAMPLE "D"

Gamma Methyl Gamma Cyclopentyl Butyrolactone

Reaction:

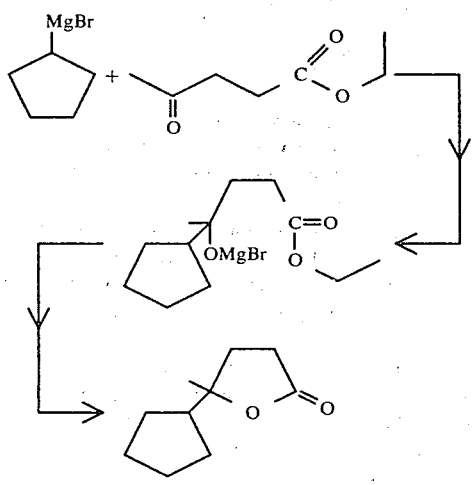

Into a 500 ml reaction flask equipped with stirrer, heating mantle, cooling bath, reflux condenser, thermometer, addition funnel and nitrogen blanket apparatus is added 300 ml anhydrous diethylether, 16 grams (0.66 moles) of magnesium turnings and an iodine crystal. Over a period of 1 hour and 20 minutes from the addition funnel is charged 100 grams (0.66 moles) of cyclopentyl bromide. After the addition of the cyclopentyl bromide, refluxing is continued while maintaining the temperature at 37°-40° C. Reflux is continued for another 6 hours. At the end of the refluxing, 200 ml diethylether is stripped off and replaced with 100 ml toluene.

Into a 1 liter reaction flask is charged 250 ml toluene and 95 grams of ethyl levulinate. The resulting mixture is cooled to −5° C. Over a period of 1 hour while maintaining the temperature at −5° C., is added the Grignard reagent (cyclopentyl magnesium bromide) produced above.

At the completion of the addition, the reaction mass is stirred for 1 hour while maintaining the temperature at −5° C.

Over a period of 1 hour while maintaining the reaction temperature at 25-35° C., a 25% aqueous solution of sulfuric acid is added to the reaction mass in order to cause the pH to be adjusted to the range of 3-4. The reaction mass is heated to 25° C. and maintained at that temperature for a period of 1 hour.

The reaction mass is then transferred to a separatory funnel and the aqueous layer is extracted with one 250 ml portion of diethylether. The organic layer is combined with the diethylether extract and the resulting combined organic layers are washed as follows:

(a) Two 250 ml portions of saturated sodium bicarbonate to a pH of 6-7;
(b) One 250 ml portion of saturated sodium chloride solution.

the resulting organic solution is then dried over anhydrous sodium sulfate and distilled on a 2" Splash column yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 35/15 | 100/20 | 100 | 3.7 |
| 2 | 88 | 100 | 10 | 10 |
| 3 | 116 | 145 | 10 | 2.1 |
| 4 | 128 | 200 | 10 | 9.7 |

The resulting product (bulked Fractions 2, 3 and 4) has a fruity (apple), sweet, cinnamic aroma with animal-like undertones.

The resulting material has a woody, blue cheese-like, coumarin-like aroma and taste with lemon fresh back-notes at 10 ppm cuasing it to be useful in coconut flavors.

FIG. 9 is the GLC profile for the reaction product prior to distillation (conditions: SE-30, 10'×⅛", column programmed at 100°-220° C. at 8° C. per minute).

FIG. 10 is the GLC profile for Fraction 1 of the foregoing distillation (conditions: SE-30, 10'×⅛", column programmed at 100°-220° C. at 8° C. per minute).

FIG. 11 is the GLC profile for Fraction 2 of the foregoing distillation (conditions: SE-30, 10'×⅛", column programmed at 100°-220° C. at 8° C. per minute).

FIG. 12 is the GLC profile for Fraction 3 of the foregoing distillation (conditions: SE-30, 10'×⅛", column programmed at 100°-220° C. at 8° C. per minute).

FIG. 13 is the GLC profile for Fraction 4 of the foregoing distillation (conditions: SE-30, 10'×⅛", column programmed at 100°-220° C. at 8° C. per minute). The reference numeral "124" is indicative of the peak wherein the product is that having the structure:

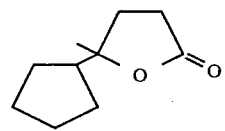

FIG. 14 is the NMR spectrum for the peak indicated by the reference numeral "124" on FIG. 13 which is the peak for the product of Fraction 4 of the foregoing distillation consisting of the compound having the structure:

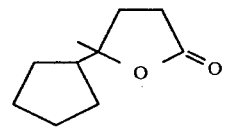

EXAMPLE I

Herbal Fragrances

The following mixtures are prepared:

| Ingredients | Parts by Weight | |
|---|---|---|
| | I(A) | I(B) |
| Amyl cinnamic aldehyde | 20 | 20 |
| Phenyl acetaldehyde dimethyl acetal | 4 | 4 |
| Thyme oil white | 8 | 8 |
| Sauge sclaree French | 8 | 8 |
| Galbanum oil | 4 | 4 |
| Geranyl acetate | 10 | 10 |
| Juniper berry oil | 4 | 4 |
| Methyl octynyl carbonate | 2 | 2 |
| Linalyl acetate | 10 | 10 |
| Dihydro methyl jasmonate | 20 | 20 |
| Gamma methyl gamma cyclohexyl butyrolactone prepared according to Example "C" | 0 | 12 |
| Limonene carboxaldehyde prepared according to Example "A" | 12 | 12 |

A limonene carboxaldehyde prepared according to Example "A" adds a strong, sweet, bready, lactonic undertone with milky, almond and cumin-like nuances to this herbal fragrance formulation. The gamma methyl gamma cyclohexyl butyrolactone prepared according to Example "C" also adds a strong, herbaceous, coumarin-like, mossy, strong tonka-like, fig leaf absolute-like, tolu absolute-like, sweet characterisics to this herbal fragrance formulation. d

EXAMPLE II

Production of Lilac Fragrances

The following mixtures are prepared:

| Ingredients | Parts by Weight | |
|---|---|---|
| | II(A) | II(B) |
| Hydroxycitronella | 22 | 22 |
| Phenylethyl alcohol | 12 | 12 |
| Heliotropine | 12 | 12 |
| Linalool | 8 | 8 |
| Cinnamic alcohol | 4 | 4 |
| Indol (10% in diethyl phthalate) | 2 | 2 |
| Benzyl acetate | 8 | 8 |
| Anisic alcohol | 8 | 8 |
| Coumarin (10% in diethyl phthalate) | 4 | 4 |
| Benzyl alcohol | 16 | 16 |
| Gamma methyl gamma cyclopentyl butyrolactone prepared according to Example "D" | 0 | 4 |
| Limonene carboxaldehyde prepared according to Example "B" | 6 | 6 |

The limonene carboxaldehyde prepared according to Example "B" adds to this lilac fragrance an interesting coconut-like, citrusy topnote. The gamma methyl gamma cyclopentyl butyrolactone adds a fruity, cinnamon-like nuance with animal undertones to this lilac fragrance.

EXAMPLE III

Preparation of a Cosmetic Powder Composition

A cosmetic powder is prepared by mixing in a ball mill 100 grams of talcum powder with 0.25 grams of the perfume substance set forth in Table I below. The resulting cosmetic powders have excellent aroma profiles as indicated in Table I below:

TABLE I

| Perfume Substance | Aroma Profile Imparted |
|---|---|
| Limonene carboxaldehyde mixture of isomers having the structures: 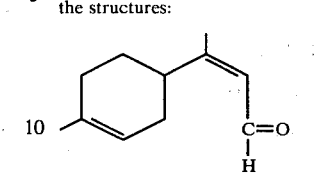 and ... prepared according to Example "A" (50:50 E:Z isomer mixture) | A sweet, bready-like, lactonic, aroma with milky, almond-like, and cumin undertones. |
| Limonene carboxaldehyde mixture having the structures: ... and ... prepared according to Example "B" (E:Z ratio: 1:40) | A coconut-like, orange blossom aroma profile. |
| 50:50 (mole ratio) mixture of limonene carboxaldehyde of Example "B" and gamma methyl gamma cyclohexyl butyrolactone prepared according to Example "C". | An orange-like, coconut-like, sweet, coumarin-like, mossy, strong tonka-like, tolu absolute-like, fig leaf absolute-like, benzoin-like aroma with green, herbaceous undertones and animal topnotes. |
| 50:50 (mole ratio) mixture of limonene carboxaldehyde prepared according to Example "B" and gamma methyl gamma cyclopentyl butyrolactone prepared according to Example "D". | A coconut-like, orange-like, fruity (apple), sweet, cinnamic-like aroma with animal undertones and woody topnotes. |
| Perfume composition of Example I(A). | A herbal fragrance with sweet, bready, lactonic, milky, almond-like and cumin undertones. |
| Perfume composition of Example I(B). | A herbal fragrance with sweet, bready, lactonic, milky, almond, cumin-like, fig leaf, tonka-like, mossy, tolu absolute-like undertones. |
| Perfume composition of Example II(A). | Lilac aroma with coconut-like and orange blossom-like undertones. |
| Perfume composition of Example II(B). | Lilac aroma with coconut-like, orange-like topnotes and fruity, cinnamon-like, |

TABLE I-continued

| Perfume Substance | Aroma Profile Imparted |
|---|---|
| | animalic undertones. |

EXAMPLE IV

Preparation of Soap Composition 100 grams of soap chips are mixed with 1 gram of each of the perfume materials of Table I of Example III until a substantially homogeneous composition is obtained. The resulting mixture is melted and maintained at 10 atmospheres pressure at a temperature of 180° C. for a period of 4 hours. At the end of the 4 hour period, the resulting homogeneous mixture is cooled. The perfumed soap composition manifests an excellent aroma character as set forth in Table I of Example III.

EXAMPLE V

Preparation of a Detergent Composition

A granular detergent composition is prepared according to Example IX of Canadian Patent No. 1,004,566 (the disclosure of which is incorporated by reference herein) containing the following ingredients:

| Component | Weight % |
|---|---|
| Anhydrous sodium carbonate | 30.0 |
| Hydrated sodium silicate (81.5% solids, $SiO_2:Na_2O$ ratio-2.1:1 by weight) | 20.0 |
| Coconut alcohol condensed with 6 molar proportions of ethylene oxide | 10.0 |
| Sodium citrate dihydrate | 10.0 |
| Sodium dichlorocyanurate dihydrate | 3.8 |
| Polyethylene glcyol (available under the trademark Carbowax 4000, M.W. 3000-3700) | 2.0 |
| Dimethyl silicone | 0.8 |
| Anhydrous sodium sulfate | 15.5 |
| Perfume substance as set forth in Table I of Example III | 5.9 |

The resulting detergent compositions have excellent aromas as set forth in Table I of Example III.

EXAMPLE VI

Preparation of a Detergent Composition

A detergent is prepared from the following ingredients according to Example I of Canadian Patent No. 1,007,948 (the disclosure of which is incorporated herein by reference):

| Ingredients | Parts by Weight |
|---|---|
| Neodol 45-11 (a $C_{14}14$ $C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. A total of 100 grams of this detergent is admixed individually with 0.15 grams of each of the perfumery substances of Table I of Example III. Each of the detergents has excellent aromas as set forth in Table I of Example III.

EXAMPLE VII

Perfumed Liquid Detergent

Concentrated liquid detergents with aroma nuances as set forth in Table I of Example III containing 0.10%, 0.15% and 0.20% of each of the perfumery substances of Table I of Example III are prepared. They are prepared by adding and homogeneously admixing the appropriate quantity of each of the perfumery substances of Table I of Example III in the liquid detergent. The degergents all possess excellent aromas as set forth in Table I of Example III.

EXAMPLE VIII

Cologne and Handkerchief Perfumes

The perfume substances of Table I of Example III are each incorporated separately into colognes at concentrations of 1.5%, 2.0%, 2.5%, 3.0%, 4.0% and 5.0% in 70%, 75%, 80%, 85%, and 90% aqueous ethanol solutions; and into handkerchief perfumes at concentrations of 15%, 20%, 30% and 40% (in 80%, 85%, 90% and 95% aqueous ethanol solutions). Distinct and definitive strong fragrances are imparted to the colognes and to the handkerchief perfumes at the levels indicated according to the aroma profiles as set forth in Table I of Example III.

EXAMPLE IX

Perfumed Plastics

Scented polyethylene pellets having pronounced aromas as set forth in Table I of Example III are prepared as follows:

Seventy-five pounds of polyethylene having a melting point of about 220° F is heated to about 230° F. in a container of the kind illustrated in FIGS. 4 and 5. Twenty-five pounds of the fragrance materials of Table I of Example III is then quickly added to the liquified polyethylene, the lid 528 is put in place and the agitating means 573 are actuated. The temperature is maintained at about 225° F. and the mixing is continued for about 5-15 minutes. The valve "V" is then opened to allow flow of the molten polyethylene enriched with the aroma containing material to exit through the orifices 534. The liquid falling through the orifices 534 solidifies almost instantaneously upon impact with the moving cooled conveyor 538. Polyethylene beads or pellets 544 having promounced aromas as set forth in Table I of Example III are thus formed. Analysis demonstrates that the pellets contain about 25% of the aroma substance of Table I of Example III so that almost no loss in the scenting substance occur. These pellets may be called "master pellets".

Fifty pounds of the aroma substance-containing master pellets are then added to one thousand pounds of unscented polyethylene powder and the mass is heated to a liquid state. The liquid is molded into thin sheets of films. The thin sheets of films have pronounced aromas as set forth in Table I of Example III. The sheets of films are cut into strips ¼" in width ×3 " in length and employed in standard air freshening apparatus.

On operation of the standard air freshening apparatus as a room air freshener, after four minutes, the room has an aesthetically pleasing aroma as set forth in Table I of Example III with no foul odor being present.

EXAMPLE X

One hundred pounds of polypropylene are heated to about 300° F. Thirty pounds of the essence of the perfume substances is described in Table I of Example III, supra, are added to the liquified polypropylene. The procedure is carried out in the apparatus shown in FIGS. 4 and 5. After mixing for about eight minutes, the valve "V" is opened to allow the exit of polypropylene scented material mixture whereby solid pellets having a pronounced perfume smell are formed on the conveyor. The pellets thus obtained are then admixed with about twenty times their weight of unscented polypropylene and the mixture is heated and molded into "spaghetti" tows. The spaghetti tows are cut into small cylinders approximately 0.1 inches in length ×0.02 inches in diameter. The cylinders have a strong and pleasant perfumed smell and scent as set forth in Table I of Example III, supra.

The cylinders are used in standard air freshening apparatus to produce aesthetically pleasing faint scent with no foul odor in environments surrounding the air freshening apparatus the scents described in Table I of Example III, supra.

EXAMPLE XI

Coconut Flavors

The following basic coconut flavor is prepared:

| Ingredients | Parts by Weight |
| --- | --- |
| 2,5-dimethyl-3-hydroxy-4,5-dihydrofuran-4-one | 4.0 |
| 2-methyl-5-ethylfuran | 0.3 |
| 2-acetylfuran | 2.0 |
| almond oil | 1.2 |
| vanillin natural | 12.0 |
| gamma nonalactone | 3.0 |
| delta dodecalactone | 4.8 |
| maltol | 3.2 |

This flavor formulation is divided into 3 portions. 8 Parts by weight of the first portion is combined with 2 parts by weight of limonene carboxaldehyde isomer mixture prepared according to Example "A".

8 Parts by weight of the second portion is combined with 2 parts by weight of limonene carboxaldehyde prepared according to Example "B".

Nothing is added to the third part.

The three flavors are compared in water at the rate of 10 ppm and evaluated by a bench panel. The two flavors containing the limonene carboxaldehydes produced according to Examples "A" and "B" produce in addition to a fuller coconut related note, a sweet, fruity, citrusy note. The flavors are useful in preparing a "pina colada" beverage as set forth in Example XII, infra.

Therefore, the flavors containing the limonene carboxaldehydes are considered by the bench panel as better and more suitable flavors for synthetic coconut flavors having unique flavor effects and having the ability to be combined with natural coconut milk in order to retard spoilage.

Spoilage in natural coconut milk is prevented while maintaining the coconut milk at 40° F. for a period of 10 days.

EXAMPLE XII

A "pina colada" mix is prepared by intimately admixing 4 grams of limonene carboxaldehyde prepared according to Example "A" and 4 grams of limonene carboxaldehydes prepared according to Example "B" together with 10 grams of coconut milk, natural. The resulting mixture is admixed with 50 grams of xanthan gum and the resulting emulsion is spray-dried with a Bowen Lab Model Drier utilizing 260 cfm of air with an inlet temperature of 500° F., an outlet temperature of 200° F. and a wheel speed of 50,000 rpm. The resulting powder is then intimately admixed with a standard "pina colada" alcoholic beverage. The resulting beverage has a much more natural coconut flavor than the standard "pina colada" alcoholic beverage taken alone.

EXAMPLE XIII

A. Powder Flavor Composition 20 grams of the flavor composition of Example XI is emulsified in a solution containing 300 grams of gum acacia and 700 grams of water. The emulsion is spray-dried with a Bowen Lab Model Drier utilizing 260 cfm of air with an inlet temperature of 500° F., an outlet temperature of 200° F. and a wheel speed of 50,000 rpm.

B. Sustained Release Flavor

The following mixture is prepared:

| Ingredients | Parts by Weight |
| --- | --- |
| Liquid coconut flavor containing one of the gamma methyl gamma cycloalkyl butyrolactones of Example XI | 20.0 |
| Propylene glycol | 9.0 |
| Cab-O-Sil ® M-5 (brand of silica produced by the Cabot Corporation, 125 High St., Boston, Mass. 02110 Physical properties: Surface Area: 200 m²/gm Nominal particle size: 0.012 microns Density: 2.3 lbs/cu. ft.) | 5.0 |

The Cab-O-Sil ® is dispersed in the liquid coconut flavor composition of Example XI with vigorous stirring thereby resulting in a viscous liquid. 71 Parts by weight of the powder flavor composition of Part A, supra, is then blended into the said viscous liquid with stirring at 25° C. for a period of 30 minutes resulting in a dry, free-flowing, sustained release flavor powder.

EXAMPLE XIV

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example XI (containing one of the limonene carboxaldehydes prepared according to Example A or Example B) is added to the solution which is then homogenized to form an emulsion having a particle size typically in the range of 5–40 microns. The material is kept at 120° F. under which conditions the gelatin will not gel.

Coacervation is induced by adding, slowly and uniformly, 40 parts by weight of 20% aqueous solution of sodium sulfate. During coacervation, the gelatin molecules are deposited uniformly about each oil droplet as a nucleus.

Gelation is effected by pouring the heated coacervate mixture into 1,000 parts by weight of 7% aqueous solution of sodium sulfate at 65° F. The resulting gelled coacervate may be filtered and washed with water at temperatures below the melting point of gelatin to remove the salt.

Hardening of the filtered cake in this example is effected by washing with 200 parts by weight of 30% solution of formaldehyde in water. The cake is then thoroughly washed with water to remove the residual formaldehyde.

EXAMPLE XV

Chewing Gum

100 Parts by weight of chicle are mixed with 4 parts by weight of the flavor prepared in accordance with Example XIII. 300 Parts Sucroses and 100 parts corn syrup are added. Mixing is effected in a ribbon blender with jacketed side walls of the type manufactured by the Baker Perkins Company.

The resultant chewing gum blend is then manufactured into strips 1 inch in width and 0.1 inches in thickness. The strips are cut into lengths of 3 inches each. On chewing, the chewing gum has a pleasant, long-lasting, coconut flavor.

EXAMPLE XVI

Chewing Gum

100 Parts by weight of chicle are mixed with 18 parts by weight of the flavor prepared in accordance with Example XIII, Part B. 300 Parts of sucrose and 100 parts of corn syrup are then added. Mixing is effected in a ribbon blender with jacketed side walls of the type manufactured by the Baker Perkins Company.

The resultant chewing gum blend is then manufactured into strips 1 inch in width and 0.1 inches in thickness. The strips are cut into lengths of 3 inches each. On chewing, the chewing gum has a pleasant, very long-lasting coconut flavor.

EXAMPLE XVII

Toothpaste Formulation

The following separate groups of ingredients are prepared:

| Parts by Weight | Ingredients |
|---|---|
| Group "A" | |
| 30.200 | Glycerine |
| 15.325 | Distilled water |
| .100 | Sodium benzoate |
| .125 | Saccharin sodium |
| .400 | Stannous fluoride |
| Group "B" | |
| 12.500 | Calcium carbonate |
| 37.200 | Dicalcium phosphate (dihydrate) |
| Group "C" | |
| 2.000 | Sodium n-lauroyl sarcosinate (foaming agent) |
| Group "D" | |
| 1.200 | Flavor material of Example XIII, Part B |
| 100.000 (total) | |

Procedure:

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing, until a homogeneous paste is formed.
4. With stirring, the flavor of "D" is added and lastly the sodium n-lauroyl sarcosinate.
5. the resultant slurry is then blended for one hour. The completed paste is then transferred to a three roller mill and then homogenized, and finally tubed.

The resulting toothpaste when used in a normal toothbrushing procedure yields a pleasant coconut flavor of constant strong intensity throughout said procedure (1–1.5 minutes).

EXAMPLE XVIII

Chewable Vitamin Tablets

The flavor material produced according to the process of Example XIII, Part B, is added to a chewable vitamin tablet formulation at a rate of 10 grams per kilogram which chewable vitamin tablet formulation is prepared as follows:

In a Hobart Mixer, the following materials are blended to a homogeneity:

| | Gms/1000 tablets |
|---|---|
| Vitamin C (ascorbid acid) as ascorbic acid-sodium ascorbate mixture 1:1 | 70.11 |
| Vitamin $B_1$ (thiamine mononitrate) as Rocoat ® thiamine mononitrate 33⅓% (Hoffman La Roche) | 4.0 |
| Vitamin $B_2$ (riboflavin) as Rocoat ® riboflavin 33⅓% | 5.0 |
| Vitamin $B_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-biotin | 0.144 |
| Flavor of Example XIII, Part B | (as indicated above) |
| Certified lake color | 5.0 |
| Sweetener - sodium saccharin | 1.0 |
| Magnesium stearate lubricant | 10.0 |
| Mannitol, q.s. to make | 500.00 |

Preliminary tablets are prepared by slugging with flat faced punches and grinding the slugs to 14 mesh. 13.5 Grams dry Vitamin A acetate and 0.6 grams Vitamin D are then added as beadlets. The entire blend is then compressed using concave punches at 0.5 grams each.

Chewing of the resultant tablets yields a pleasant, longlasting, consistently strong coconut flavor for a period of 12 minutes.

EXAMPLE XIX

Cocnut Macaroon

A standard almond paste coconut macaroon cookie is preparred whereby immediately prior to placing the paste into molds for the purposes of baking, the mix is intimately admixed with one of the limonene carboxaldehydes prepared according to Example A or B or a 50:50 mixture of the methyl gamma cycloalkyl butyrolactones prepared according to Examples C and D: limonene carboxaldehydes prepared according to Examples A or B at the rates of 20 ppm, 25 ppm, 30 ppm, 50 ppm and 80 ppm. The resulting molded pastes are then baked to yield toasted macaroon cookies. The toasted macaroon cookies are much more natural coconut-like than those produced without the limonene carboxaldehyes prepared according to Examples A and B and are preferred by a 4-member bench panel of experts.

The coconut macaroon cookies are of the type distributed by Drake Bakeries, Division of Borden, Inc. of Columbus, Ohio having the ingredients:

Corn syrup
Coconut
Sucrose
Egg whites
Corn starch
Sodium chloride
Sodium carbonate
Water
Sodium acid pyrophosphate,
Monocalcium phosphate and
Calcium sulfate weighing 0.56 ozs. each.

What is claimed is:

1. A process for augmenting or enchancing the aroma or taste of a consumable material selected from the group consisting of foodstuffs and chewing gums comprising the step of adding to said consumable material from 0.2 ppm up to about 100 ppm based on total composition of a mixture of isomers in the ratio of 50:50 defined according to the structures:

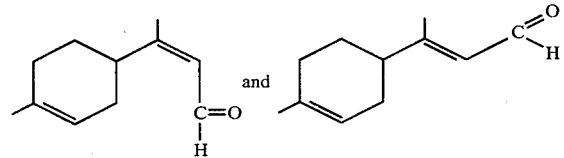

prepared by reacting the salt having the structure:

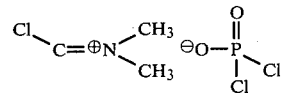

with limonene to form a complex and reacting the resulting complex with aqueous base in accordance with the reaction sequence:

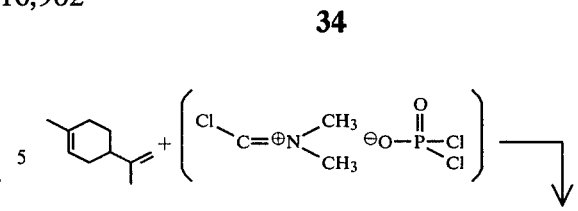

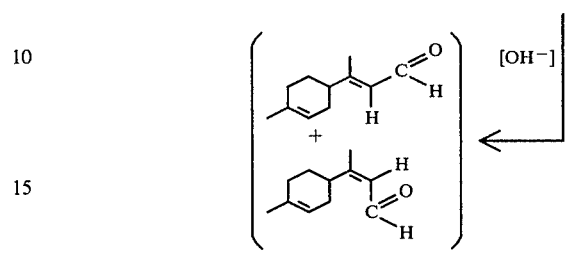

2. A process for augmenting or enhancing the aroma or taste of a consumable material selected from the group consisting of foodstuffs and chewing gums comprising the step of adding to said consumable material from 0.5 ppm up to about 100 ppm of a mixture of isomers in the ratio of 1:40 having the structures:

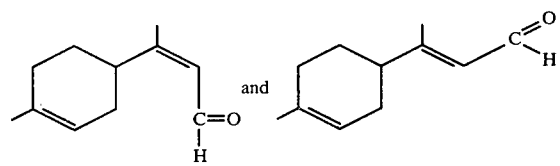

produced according to the process of first reacting limonene with chlorine in the presence of light to form limonene chloride; then reacting the limonene chloride with a nitrile to form a limonene nitrile; then reacting the limonene nitrile with a lower alkyl aluminum hydride according to the reaction sequence:

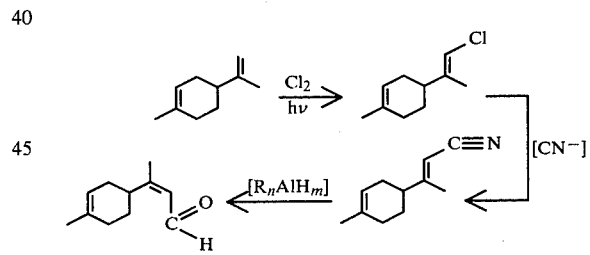

wherein R is lower alkyl, and wherein n is 1 or 2 and m is 1 to 2 and the sum of m+n is 3.

* * * * *